(12) United States Patent
Kugler et al.

(10) Patent No.: US 7,112,217 B1
(45) Date of Patent: Sep. 26, 2006

(54) BILUMINAL ENDOVASCULAR GRAFT SYSTEM

(75) Inventors: Chad J. Kugler, Andover, MN (US); John R. Drontle, Monticello, MN (US); Peter T. Keith, St. Paul, MN (US); Thomas V. Ressemann, St. Cloud, MN (US); Matthew J. Olson, Roseville, MN (US); Thomas K. Heiland, Brooklyn Park, MN (US)

(73) Assignee: Cordis Corporation, Miami Lakes, FL (US)

( * ) Notice: Subject to any disclaimer, the term of this patent is extended or adjusted under 35 U.S.C. 154(b) by 79 days.

(21) Appl. No.: 09/652,548

(22) Filed: Aug. 31, 2000

Related U.S. Application Data

(62) Division of application No. 09/039,776, filed on Mar. 16, 1998, now Pat. No. 6,129,756.

(51) Int. Cl.
*A61F 2/06* (2006.01)
(52) U.S. Cl. ............. 623/1.31; 623/1.13; 623/1.35
(58) Field of Classification Search ............. 623/1.16, 623/1.21, 1.28, 1.3, 1.31, 1.35, 1.23, 1.32, 623/1.13
See application file for complete search history.

(56) References Cited

U.S. PATENT DOCUMENTS

| | | | |
|---|---|---|---|
| 3,657,744 A | 4/1972 | Ersek | |
| 4,140,126 A | 2/1979 | Choudhury | |
| 4,503,569 A | 3/1985 | Dotter | |
| 4,512,338 A | 4/1985 | Balko et al. | |
| 4,562,596 A | 1/1986 | Kornberg | |
| 4,577,631 A | 3/1986 | Kreamer | |
| 4,617,932 A | 10/1986 | Kornberg | |
| 4,655,771 A | 4/1987 | Wallsten | |
| 4,665,906 A | 5/1987 | Jervis | |
| 4,733,665 A | 3/1988 | Palmaz | |
| 4,739,762 A | 4/1988 | Palmaz | |
| 4,787,899 A | 11/1988 | Lazarus | |
| 4,878,906 A | 11/1989 | Lindemann et al. | |
| 4,994,071 A | 2/1991 | MacGregor | |
| 5,067,957 A | 11/1991 | Jervis | |
| 5,078,726 A | 1/1992 | Kreamer | |
| 5,104,399 A | 4/1992 | Lazarus | |
| 5,122,154 A | 6/1992 | Rhodes | |
| 5,123,917 A | 6/1992 | Lee | |
| 5,190,546 A | 3/1993 | Jervis | |

(Continued)

FOREIGN PATENT DOCUMENTS

EP 536164 3/1994

(Continued)

OTHER PUBLICATIONS

Choo, M.D. et al., "Malignant Colorectal Obstruction: Treatment with a Flexible Covered Stent", *Radiology*, 206:415-421, 1998.

(Continued)

*Primary Examiner*—Corrine McDermott
*Assistant Examiner*—William H Matthews

(57) ABSTRACT

An endovascular graft system used to repair aneurysms in arteries which bifurcate such as the aorta which bifurcates at the aortoiliac junction. The graft system includes two legs, each defining a lumen. Each leg comprises an aortic stent, a graft component and an iliac stent. The graft component is affixed at one end to the aortic stent and at the other end to the iliac stent. Each leg of the graft system is preferably a mirror image of the other with the exception of the aortic stents. The graft component of each leg includes a means for allowing in situ adjustment of the length of the leg to accommodate the different sizes required for different patients.

3 Claims, 28 Drawing Sheets

U.S. PATENT DOCUMENTS

| | | | |
|---|---|---|---|
| 5,275,622 A | 1/1994 | Lazarus et al. | |
| 5,316,023 A | 5/1994 | Palmaz et al. | |
| 5,360,443 A | 11/1994 | Barone et al. | |
| 5,383,892 A | 1/1995 | Cardon et al. | |
| 5,387,235 A | 2/1995 | Chuter | |
| 5,395,390 A | 3/1995 | Simon et al. | |
| 5,397,345 A | 3/1995 | Lazarus | |
| 5,397,355 A | 3/1995 | Marin et al. | |
| 5,403,378 A | 4/1995 | Wells et al. | |
| 5,405,378 A | 4/1995 | Strecker | |
| 5,443,477 A | 8/1995 | Marin et al. | |
| 5,449,373 A | 9/1995 | Pinchasik et al. | |
| 5,456,694 A | 10/1995 | Marin et al. | |
| 5,456,713 A | 10/1995 | Chuter | |
| 5,476,506 A * | 12/1995 | Lunn | 623/1.31 |
| 5,489,295 A | 2/1996 | Piplani et al. | |
| 5,507,769 A | 4/1996 | Marin et al. | |
| 5,522,880 A | 6/1996 | Barone et al. | |
| 5,540,712 A | 7/1996 | Kleshinski et al. | |
| 5,540,713 A | 7/1996 | Schnepp-Pesch et al. | |
| 5,562,724 A | 10/1996 | Vorwerk et al. | |
| 5,562,728 A | 10/1996 | Lazarus et al. | |
| 5,569,296 A | 10/1996 | Marin et al. | |
| 5,578,071 A | 11/1996 | Parodi | |
| 5,578,072 A | 11/1996 | Barone et al. | |
| 5,591,196 A | 1/1997 | Marin et al. | |
| 5,591,228 A | 1/1997 | Edoga | |
| 5,593,417 A | 1/1997 | Rhodes | |
| 5,597,378 A | 1/1997 | Jervis | |
| 5,609,625 A | 3/1997 | Piplani et al. | |
| 5,609,627 A | 3/1997 | Goicoechea et al. | |
| 5,628,783 A | 5/1997 | Quiachon et al. | |
| 5,639,278 A | 6/1997 | Dereume et al. | |
| 5,653,743 A | 8/1997 | Martin | |
| 5,653,748 A | 8/1997 | Strecker | |
| 5,662,675 A | 9/1997 | Polanskyj Stockert et al. | |
| 5,662,700 A | 9/1997 | Lazarus | |
| 5,669,936 A | 9/1997 | Lazarus | |
| 5,676,696 A | 10/1997 | Marcade | |
| 5,683,449 A | 11/1997 | Marcade | |
| 5,693,083 A | 12/1997 | Baker et al. | |
| 5,693,084 A | 12/1997 | Chuter | |
| 5,693,089 A | 12/1997 | Inoue | |
| 5,716,365 A | 2/1998 | Goicoechea et al. | |
| 5,723,003 A | 3/1998 | Winston et al. | |
| 5,723,004 A | 3/1998 | Dereume et al. | |
| 5,755,778 A | 5/1998 | Kleshinski | |
| 5,769,887 A | 6/1998 | Brown et al. | |
| 5,776,161 A | 7/1998 | Globerman | |
| 5,776,181 A | 7/1998 | Lee et al. | |
| 5,782,909 A | 7/1998 | Quiachon et al. | |
| 5,800,515 A | 9/1998 | Nadal et al. | |
| 5,810,870 A | 9/1998 | Myers et al. | |
| 5,817,126 A | 10/1998 | Imran | |
| 5,824,039 A | 10/1998 | Piplani et al. | |
| 5,824,040 A | 10/1998 | Cox et al. | |
| 5,824,044 A | 10/1998 | Quiachon et al. | |
| 5,843,160 A | 12/1998 | Rhodes | |
| 5,843,167 A | 12/1998 | Dwyer et al. | |
| 5,851,228 A | 12/1998 | Pinheiro | |
| 5,919,225 A | 7/1999 | Lau et al. | |
| 5,938,697 A | 8/1999 | Killion et al. | |
| 5,993,481 A * | 11/1999 | Marcade et al. | 623/1.35 |
| 6,004,347 A | 12/1999 | McNamara et al. | |
| 6,013,854 A | 7/2000 | Moriuchi | |
| 6,102,940 A | 8/2000 | Robichon et al. | |
| 6,120,534 A * | 9/2000 | Ruiz | 623/1.31 |
| 6,123,722 A * | 9/2000 | Fogarty et al. | 623/1.31 |
| 6,124,523 A * | 9/2000 | Banas et al. | 623/1.31 |
| 6,293,969 B1 * | 9/2001 | Chuter | 623/1.31 |
| 6,302,908 B1 * | 10/2001 | Parodi | 623/1.31 |

FOREIGN PATENT DOCUMENTS

| | | |
|---|---|---|
| WO | 92/00043 | 1/1992 |
| WO | 95/08966 | 6/1995 |
| WO | 97/17910 | 5/1997 |

OTHER PUBLICATIONS

Chuter, "A Telescopic Stent-graft for Aortoiliac Implantation", *Eur. J. Vasc. Endovasc. Surg.*, 13:79-84, 1997.

Cragg, M.D. et al., "Nonsurgical Placement of Arterial Endoprosthesis: A New Technique Using Nitinol Wire[1]", *Radiology*, 147:261-263, Apr. 1983.

Dotter, M.D. et al., "Transluminal Expandable Nitinol Coil Stent Grafting: Preliminary Report[1]", *Radiology*, 147:259-260, Apr. 1983.

Weigert, M.D. et al., "Treatment of Esophagorespiratory Fistulas wirh Silicone-coated Self-expanding Metal Stents", *Gastrointestinal Endoscopy*, vol. 41, No. 5, pp. 490-496, 1995.

Choo et al., "Malignant Colorectal Obstruction: Treatment with a Flexible Covered Stent", *Radiology*, pp. 415-421 (1998).

Chuter et al., "A Telescopic Stent-graft for Aortoiliac Implantation", *Eur. J. Vasc. Endovasc. Surg.*13, pp. 79-84 (1997).

PCT International Search Report for corresponding PCT Application PCT/US99/23246.

* cited by examiner

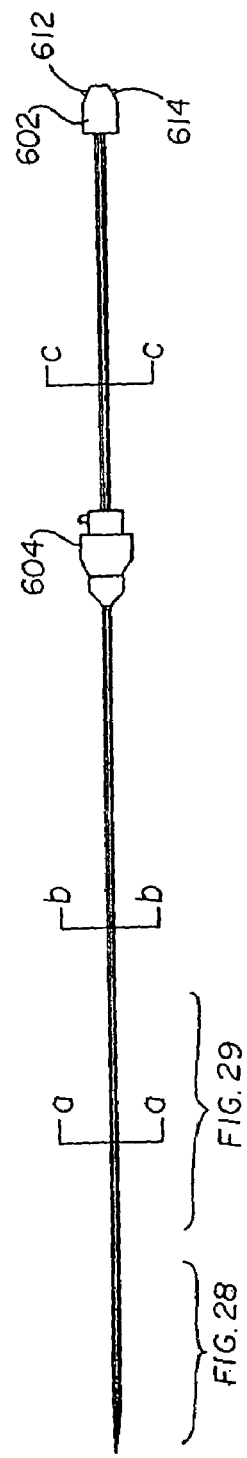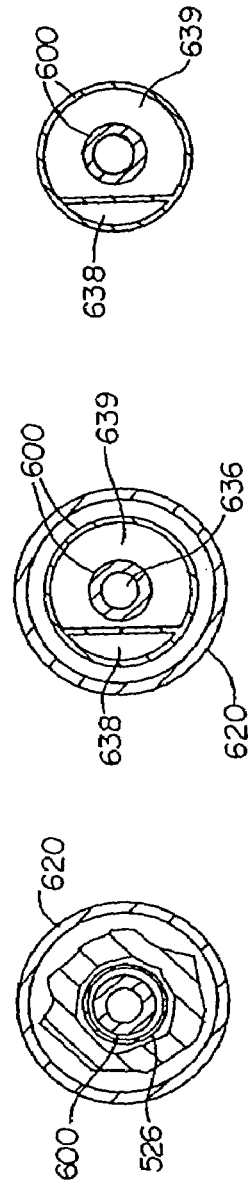

BILUMINAL ENDOVASCULAR GRAFT SYSTEM

This application is a division of U.S. Ser. No. 09/039,776, filed Mar. 16, 1998 now U.S. Pat. No. 6,129,756, the content of which is hereby incorporated herein by reference.

FIELD OF THE INVENTION

This invention relates to a graft system which is longitudinally extendible and radially expandable and to an apparatus and a method for deploying the system across an aneurysm. In particular, this invention relates to a biluminal endovascular graft system having two legs, the length of which can be adjusted in situ to obtain a correct fit for use in excluding an aneurysm.

BACKGROUND OF THE INVENTION

Aortic aneurysms represent a significant medical problem for the general population. Aneurysms within the aorta presently affect between two and seven percent of the general population and the rate of incidence appears to be increasing. This form of vascular disease is characterized by a degradation in the arterial wall in which the wall weakens and balloons outward by thinning. If untreated, the aneurysm can rupture resulting in death within a short time.

The traditional treatment for patients with an abdominal aortic aneurysm is surgical repair. This is an extensive operation involving transperitoneal or retroperitoneal dissection of the aorta and replacement of the aneurysm with an artificial artery known as a prosthetic graft. This procedure requires exposure of the aorta through an abdominal incision extending from the lower border from the breast bone down to the pubic bone. The aorta is clamped both above and below the aneurysm so that the aneurysm can be opened and the prosthetic graft of approximately the same size as the aorta is sutured in place. Blood flow is then re-established through the prosthetic graft. The operation requires a general anesthesia with a breathing tube, extensive intensive care unit monitoring in the immediate post-operative period along with blood transfusions and stomach and bladder tubes. All of this imposes stress on the cardiovascular system. This is a high-risk surgical procedure with well-recognized morbidity and mortality.

More recently, significantly less invasive clinical approaches to aneurysm repair known as endovascular grafting have been proposed. (See, Parodi, J. C., et al. "Transfemoral Intraluminal Graft Implantation for Abdominal Aortic Aneurysms," 5 Annals of Vascular Surgery, 491 (1991)). Endovascular grafting involves the transluminal placement of a prosthetic arterial graft in the endoluminal position (within the lumen of the artery). By this method, the graft is attached to the internal surface of an arterial wall by means of attachment devices such as balloon expandable stents, one above the aneurysm and a second below the aneurysm.

Although endovascular grafting represents a desirable improvement over traditional surgical repair, current endovascular graft systems suffer from certain deficiencies. For example, current endovascular graft systems do not permit in situ adjustment of length. These graft systems must either be custom ordered or many different sized grafts must be stocked by the physician in order to accommodate the varying sizes of differing patient anatomies. However, it is difficult to custom order a graft system since a patient's vascular system is three-dimensional and tortuous. Therefore, it is difficult for the physician to obtain an accurate measurement. Inventorying many different sizes of graft systems partially solves the problem but is not an acceptable solution because if the wrong size is selected the graft system cannot be modified during the procedure. Additionally, supplying differing sizes of graft systems creates inventory problems for the physician.

One method known in the art for overcoming the problem of an incorrectly sized graft is the use of a separate tubular component to extend a portion of the graft system. However, this requires removing the graft delivery system, opening an additional package with an additional tubular component, preparing the tubular component for insertion, and reinserting a delivery system to add the tubular component. This adds additional steps to the procedure and increases the complexity and time required to complete the repair. Additionally, current endovascular graft systems are not designed to allow a single system to treat a wide range of anatomical lengths.

A further problem associated with current endovascular graft systems is that during deployment the graft system temporarily occludes the aorta, generating a significant downward force. This force makes it difficult to accurately deploy the upper end of the graft system. Such a system is disclosed in U.S. Pat. No. 5,316,023 issued to Palmaz et al.

Thus, a need exists for an improved endovascular graft system which may be adjusted in situ to accommodate the varying vascular systems of different patients without the need to rely on the difficult and often inaccurate measurements of the physician. A need also exists for an endovascular graft system which can be deployed in a manner which does not occlude the artery, thus enhancing the ability to properly place the device.

SUMMARY OF THE INVENTION

This invention provides a graft system and a method for repairing an aneurysm in an abdominal aorta. The aorta branches into two iliac arteries.

In one aspect, this invention is a method for repairing an abdominal aneurysm in an aorta which branches into two iliac arteries with a graft system having first and second legs, each leg having a graft component and an aortic stent attached thereto, comprising: advancing each of the legs through a separate iliac artery; aligning the aortic stents relative to one another in the aorta on one side of the aneurysm, the graft component of each leg extending into a respective iliac artery across the aneurysm; and deploying the aligned aortic stents in the aorta in a manner that does not substantially occlude the aorta. Each leg may further include an iliac stent. The method then may further comprise deploying an iliac stents in a respective iliac artery. Each leg may have a first end and a second end and the length between the first and second ends of at least one of the legs may be adjustable; then the method further comprises adjusting the length of at least one of the first and second legs by positioning the second end of the leg a desired distance from the first end. At least one of the first and second legs may be provided with a bellows region, and then the method includes the step of adjusting the length of at least one of the first and second legs including expanding or contracting the bellows portion of the leg to thereby adjust the length. At least one of the first and second legs also may include a first segment and a second segment, the second segment being sized to fit within the first segment in a telescoping arrangement; then the step of adjusting further includes adjusting the relative position of the first and second segments such that the first end of the leg is a desired distance from the second.

At least one of the first and second legs may include at least one gripping stent; then the method further comprises deploying at least one gripping stent in the bellows region. In addition, at least one of the first and second legs may include at least one support stent; then the method further includes deploying at least one support stent within the second segment of the leg to maintain the relative position of the first and second segments after deployment. The graft system may be provided with a bellows region and the step of adjusting the length of the graft system may include expanding or contracting the bellows portion to thereby adjust the length.

In a second aspect, this invention is a method for repairing an abdominal aneurysm in an aorta which branches into two iliac arteries with a graft system having first and second ends, comprising: advancing the graft system through at least one iliac artery; positioning the first end of the graft system in the aorta on one side of the aneurysm, the second end of the graft system extending across the aneurysm; and deploying the first end of the graft system in the aneurysm in a manner that does not substantially occlude the aorta. The graft system may include an aortic stent attached to the first end of the graft system and the step of deploying may include expanding the aortic stent radially outwardly to secure the first end of the graft system in the aorta. The graft system may further include an iliac stent attached to the second end of the graft system; then the method further comprises deploying the iliac stent in the iliac artery. The length between the first and second ends may adjustable; then the method further comprises adjusting the length of the graft system by positioning the second end a desired distance from the first end. The graft system may include a first segment and a second segment, the second segment being sized to fit within the first segment in a telescoping arrangement; then the step of adjusting further comprises adjusting the relative position of the first and second segments such that the first end of the leg is a desired distance from the second.

In a third aspect, this invention is a method for repairing an abdominal aneurysm with a graft system having first and second legs, each leg having a graft component with first and second ends, the first leg having a first aortic stent, the second leg having a second aortic stent, the stents capable of expansion from a first delivery position to a second deployed position, comprising: advancing the first leg through the aorta to a desired location on one side of the aneurysm; deploying the first aortic stent so that it expands to its second deployed position, the first aortic stent causing the first end of the graft component to maintain a position on a first side of the aorta, the graft component of the first leg extending into a first iliac artery; advancing the second leg through the aorta to a desired location adjacent the first leg, the graft component of the second leg extending into a second iliac artery; and deploying the second aortic stent so that it expands to its second deployed position causing the first end of the second graft component to be positioned adjacent the first end of the first graft component on a second side of the aorta. Each leg further may include an iliac stent attached to the second end of the graft component; then the method further comprises deploying the iliac stents in a respective iliac artery. The length between the first and second ends of at least one of the legs may be adjustable; then the method further comprises adjusting the length of at least one of the first and second legs by positioning the second end of the leg a desired distance from the first end. At least one of the first and second legs also may be provided with a bellows region; then the step of adjusting the length of at least one of the first and second legs may include expanding or contracting the bellows portion of the leg to thereby adjust the length. At least one of the first and second legs also may include a first segment and a second segment, the second segment being sized to fit within the first segment in a telescoping arrangement; then the step of adjusting further comprises adjusting the relative position of the first and second segments such that the first end of the leg is a desired distance from the second.

In a fourth aspect, this invention is a method for placement of a biluminal endovascular graft system having two legs in a vessel of a patient's vascular system, at least one of the legs being adjustable in length, each leg having first and second attachment elements and a graft component with first and second ends, comprising: providing a single delivery catheter which contains a first leg of the graft system, the leg being adjustable in length; advancing the delivery catheter to a desired location in the vessel; manipulating the delivery catheter to secure the first end of the graft component in the vessel with the first attachment element; manipulating the delivery catheter to adjust the length of the first leg by positioning the second end of the graft a desired distance from the first end; and securing the second end of the graft in the vessel with the second attachment element. The first leg may be provided with a bellows region and wherein the step of manipulating the delivery catheter to adjust the length of the leg may include expanding or contracting the bellows portion of the leg to thereby adjust the length. The first leg may include a first segment and a second segment, the second segment being sized to fit within the first segment in a telescoping arrangement; then the step of manipulating the delivery catheter to adjust the length of the first leg further comprises adjusting the relative position of the first and second segments such that the first end of the first leg is a desired distance from the second. The first leg may include at least one gripping stent, the method further comprises deploying at least one gripping stent in the bellows region. The first leg also may include at least one support stent; then the method further includes deploying at least one support stent within the second segment of the first leg to maintain the relative position of the first and second segments after deployment.

In a fifth aspect, this invention is a method for repair of an abdominal aortic aneurysm with a graft system having a graft component defining at least one lumen adapted to extend from the aorta into at least one iliac artery, the graft component having first and second ends, comprising: providing a single delivery catheter which contains the graft system; advancing the delivery catheter to a desired location in the aorta; manipulating the delivery catheter to secure the first end of the graft component on one side of the aneurysm; manipulating the delivery catheter to adjust the length of the graft component by positioning the second end of the graft component on the other side of the aneurysm a desired distance from the first end; and securing the second end of the graft component in at least one iliac artery. The graft system may include an aortic stent and the step of manipulating the delivery catheter to secure the first end of the graft component may include expanding the aortic stent radially outwardly to secure the first end of the graft component in the aorta. The graft system further may include an iliac stent, and the step of securing the second end of the graft component may further comprise deploying the iliac stent radially outwardly to secure the second end of the graft component in the iliac artery. The graft component also may be provided with a bellows region and the step of adjusting the length of the graft component may include expanding or contracting the bellows portion of the graft component to thereby adjust the length. The graft component also may include a first segment and a second segment, the second segment being sized to fit within the first segment in a telescoping arrangement and the step of adjusting further comprises adjusting the relative position of the first and second segments such that the first end of the graft component is a desired distance from the second. The graft system may include at least one gripping stent; then the method further comprises deploying at least one gripping stent in the bellows region. The graft system may include at least one support stent, the method further includes deploying at least one support stent within the second segment of the graft component to maintain the relative position of the first and second segments after deployment.

In a sixth aspect, this invention is an intraluminal stent capable of expanding from a first delivery configuration to a second deployed configuration for placement in a vessel of a patient's vascular system, comprising: a first portion having a substantially circular cross-section in the deployed configuration; and a second portion attached to the first portion and having a substantially D-shaped cross-section in the deployed configuration. The second portion may be defined by a substantially flat alignment surface and a substantially curved surface which intersects the alignment surface along two edges and the attachment of the second portion to the first portion is at a first point which aligns with one of the edges and a second point which aligns with the other of the edges.

In a seventh aspect, this invention is a graft system for repairing an abdominal aortic aneurysm comprising a tubular graft component having a first end portion and a second end portion and a middle portion extending therebetween, wherein the cross-sectional areas of the first and second end portions is greater than the cross-sectional area of the middle portion. In addition, an aortic stent may be secured to the first end portion of the graft component. An iliac stent may be attached to the second end portion of the graft component. An aortic stent also may be attached to the first end portion of the graft component and an iliac stent may be attached to the second end portion of the graft component. The tubular graft component further may include a length adjustment element. The length adjustment element may comprise a bellows region within the middle portion. The length adjustment element may comprise a first graft component segment and a second graft component segment, the second graft component segment being sized to fit within the first graft component segment in a telescoping arrangement such that the length of the graft component can be adjusted by adjusting the relative telescopic position of the first and second segments. At least one gripping stent may be adapted to be deployed within the bellows region of the graft component. At least one support stent may be adapted to be deployed within the second segment of the graft component.

BRIEF DESCRIPTION OF THE DRAWINGS

FIG. 27 is a cross-sectional view of the delivery system used to insert and deploy the graft system of the embodiment of FIG. 14.

FIGS. 27a, 27b, and 27c are cross-sectional views taken along lines a—a, b—b, and c—c of FIG. 27.

DESCRIPTION OF THE PREFERRED EMBODIMENTS

Figure 1:
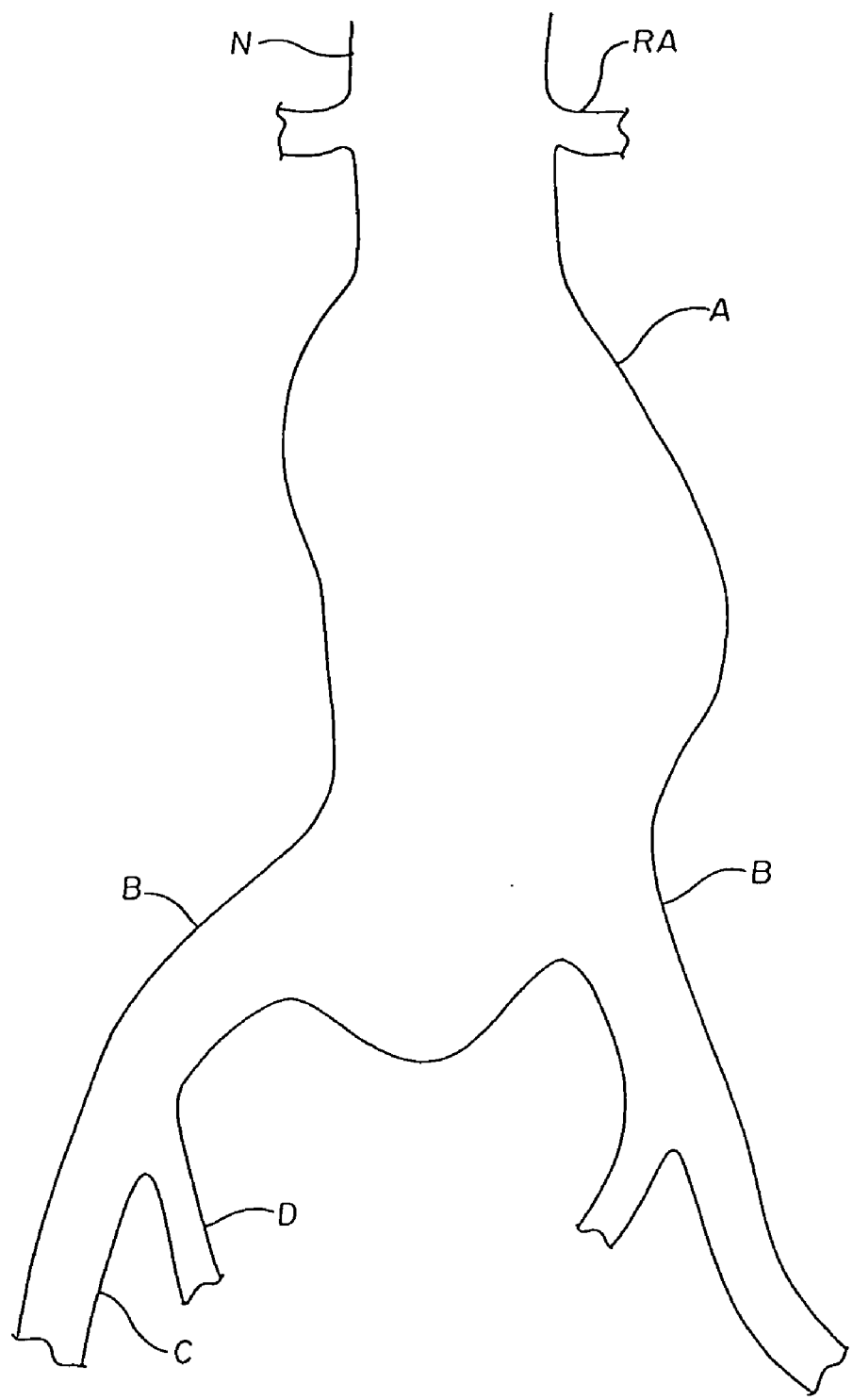
FIG. 1 is a diagrammatic view of a portion of a human vascular system depicting an abdominal aortic aneurysm which extends from below the renal arteries and into the common iliac arteries.

The terms "distal" and "proximal" as used in this specification refer only to the delivery device of the graft system, not to the vasculature. The present method contemplates advancement of a catheter in a retrograde manner (i.e., against the flow of blood). Therefore, "proximal" refers to a location closer to the physician and "distal" refers to a location farther from the physician. The vasculature is referred to with respect to the cranial (closer to head) and caudal (closer to feet) directions. Also, as used in this specification, the term "above", in the context of relative positioning with respect to the aneurysm, refers to the region cranial of the aneurysm, for example, within the aorta, whereas "below" refers to the region of the vasculature caudal of the aneurysm, for example, within the common iliac arteries.

Endovascular Graft System

The present invention provides a device and method for treating a variety of abdominal aortic aneurysms. In particular, the graft system may be used for treating aneurysms that extend close to or into the common iliac arteries. In these aneurysms there is not a suitable place within the aorta to seat the lower end of a simple tubular graft. Therefore, the graft must be able to extend into each iliac artery for suitable seating. By "seating" it is meant that the graft is implanted, fixed, or otherwise attached to the vasculature.

The endovascular graft system of the present invention is a biluminal system which may be used to repair aneurysms in arteries which bifurcate such as the aorta which bifurcates at the aortoiliac junction. The graft system comprises two legs, each defining a lumen. Each leg comprises an aortic stent, a graft component and an iliac stent. The graft component is affixed at one end to the aortic stent and at the other end to the iliac stent. Each leg of the graft system is preferably a mirror image of the other with the exception of the aortic stents. As will be seen in the drawing figures, the aortic stent of the leg oriented in the right side of the aorta (with respect to the patient) is referred to as a D-O stent whereas the leg on the left side has an aortic stent which is referred to as a D stent. Although a particular orientation of the legs within the aorta is illustrated in the drawing figures it should be understood that no particular orientation within the aorta is required, it being necessary only that the graft system be properly positioned with respect to the renal arteries and iliac arteries as discussed in more detail hereafter and that the aortic stents be properly aligned with respect to each other.

Preferably, the graft component of each leg includes a means for allowing in situ adjustment of the length of the leg to accommodate the different sizes required for different patients. This allows for a standard sized graft system (or at least fewer graft sizes) to be used which will accommodate a variety of patients. Thus, the physician is not required to inventory multiple sizes nor is the physician required to rely on measurements taken of the patients vascular system to select a particular graft size which may turn out to be incorrect. Several embodiments of the means for adjusting the length of the legs are disclosed. These embodiments include what are described as a bellows configuration, a focused bellows configuration and telescoping graft segment configuration. Each of these configurations is discussed in more detail hereafter.

FIG. 1 depicts an aneurysm A in the infrarenal aorta and extending into the common iliac arteries. The infrarenal aorta is that portion of the aorta disposed between the left and right renal arteries RA and the common iliac arteries B which branch left and right. Because bilateral symmetry is shown in the Figures, no distinction is made between elements introduced on the left or the right of the patient's vasculature. Each common iliac artery branches into internal and external iliac arteries, D and C respectively. External iliac artery C becomes the femoral artery below the inguinal ligament. Internal iliac artery D is also known as the hypogastric artery.

Figure 2:
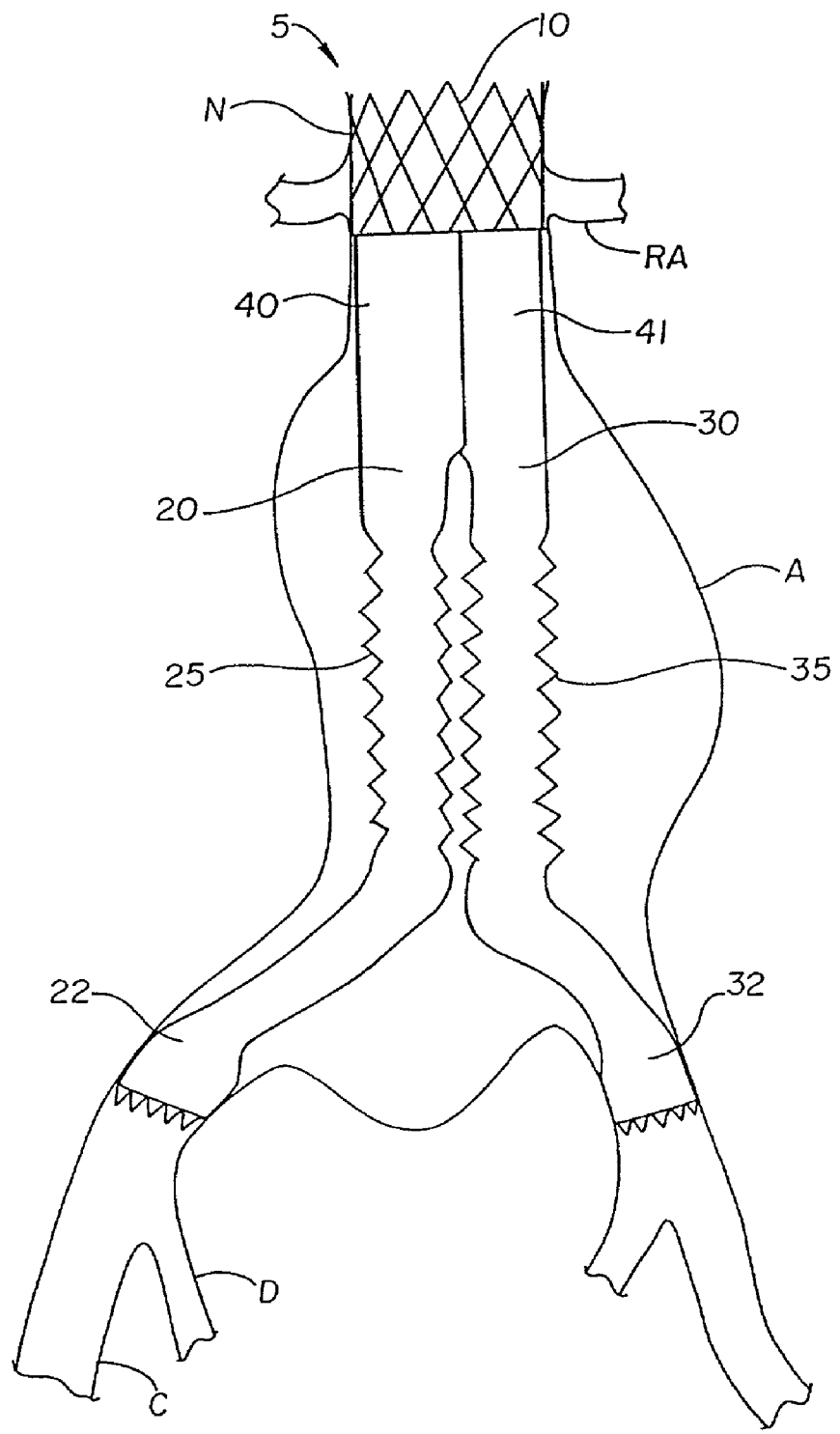
FIG. 2 is a view of the aneurysm of FIG. 1 with the legs of a first embodiment of the endovascular graft system in their fully deployed positions with full elongation of the bellows region and the caudal ends near the internal iliac branches.

FIG. 2 illustrates a first embodiment of the adjustable graft system of this invention shown deployed within aortic aneurysm A. O-shaped portion 10 of aortic stent 5 of leg 20 may be positioned in neck N of the aorta in a manner which overlaps the renal arteries, as shown. Alternatively, the top of O-shaped portion 10 may be positioned just below the renal arteries if the neck N of the aorta is sufficiently long to allow the stent to be securely affixed in that location. Legs 20 and 30 of the biluminal graft system join together in abutting relationship just below O-shaped portion 10 to form a circular shape within the lumen of the aorta as will be discussed in more detail hereafter. Bellows regions 25 and 35 are adjustable during deployment of legs 20 and 30 and held in place by gripping stents (not shown) which are described in detail hereafter. Bellows or mid regions 25 and 35 lie between upper aortic stent attachment regions and lower iliac stent attachment regions of graft components 40 and 41, respectively. Legs 20 and 30 extend from the aorta into the common iliac arteries B wherein iliac stents 22 and 32, respectively, are affixed to the arterial wall above (i.e., cranial to) the junction of the external and internal iliac arteries, C and D. The stents may be affixed by means of friction created after the stents have expanded radially outwardly, although barbs, hooks, or the like, present on the stents, are preferred means of attachment. Additionally, the stents and graft components attached to each other, preferably by means of sutures.

Figure 3:
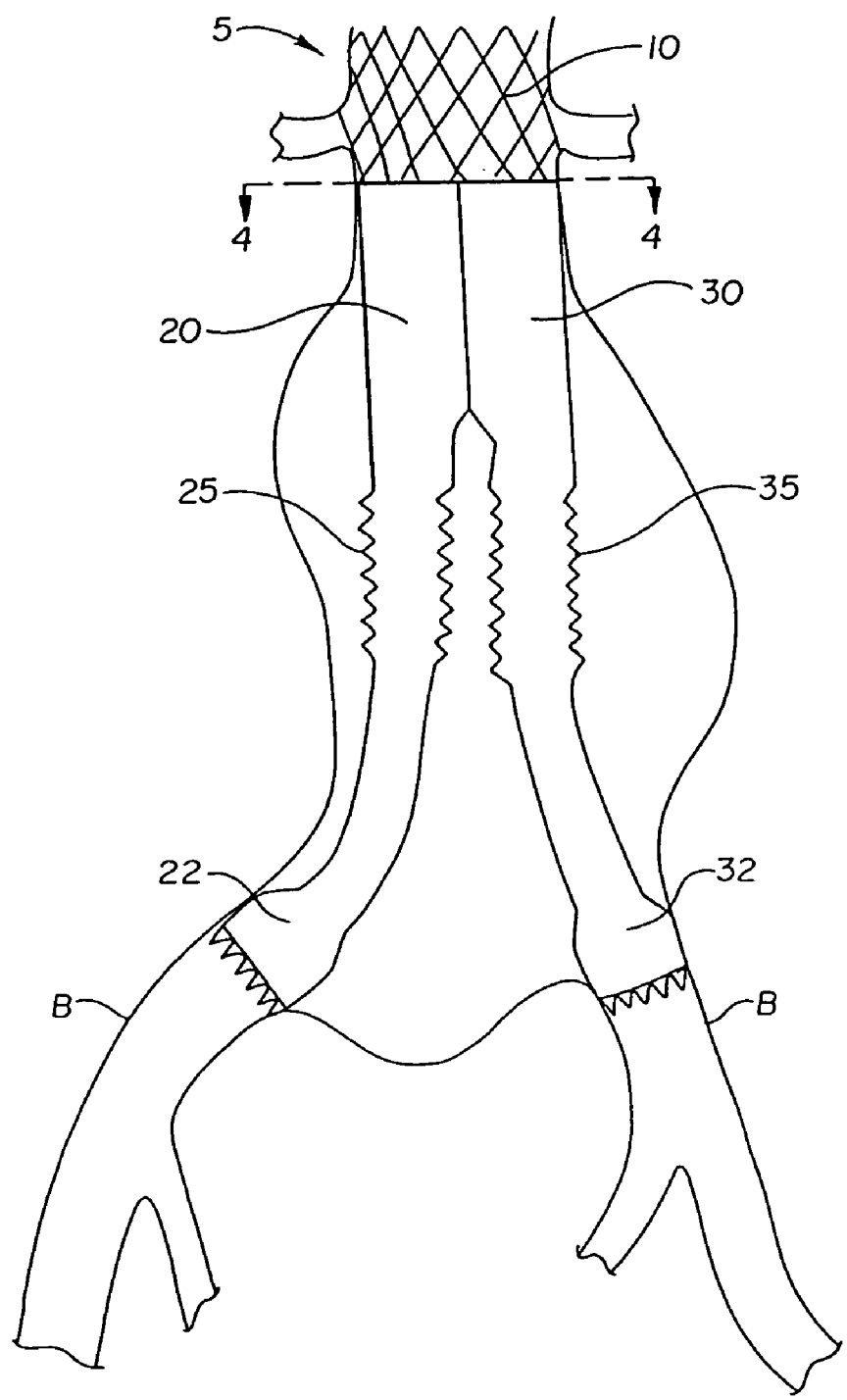
FIG. 3 is a view similar to FIG. 2 with the legs of the graft system in their fully deployed positions with a shortened (compressed) bellows region and the caudal ends farther from the internal iliac branches.

FIG. 3 illustrates the extendible graft system of FIG. 2 deployed within an aortic aneurysm A which does not extend as extensively into common iliac arteries B. Thus, iliac stents 22 and 32 are positioned at a location which is considerably cranial with respect to their position in FIG. 2. As such, bellows regions 25 and 35 are compressed compared to bellows regions 25 and 35 shown in FIG. 2. As in FIG. 2, O-shaped portion 10 of aortic stent 5 is positioned overlapping the renal arteries.

Figure 4:
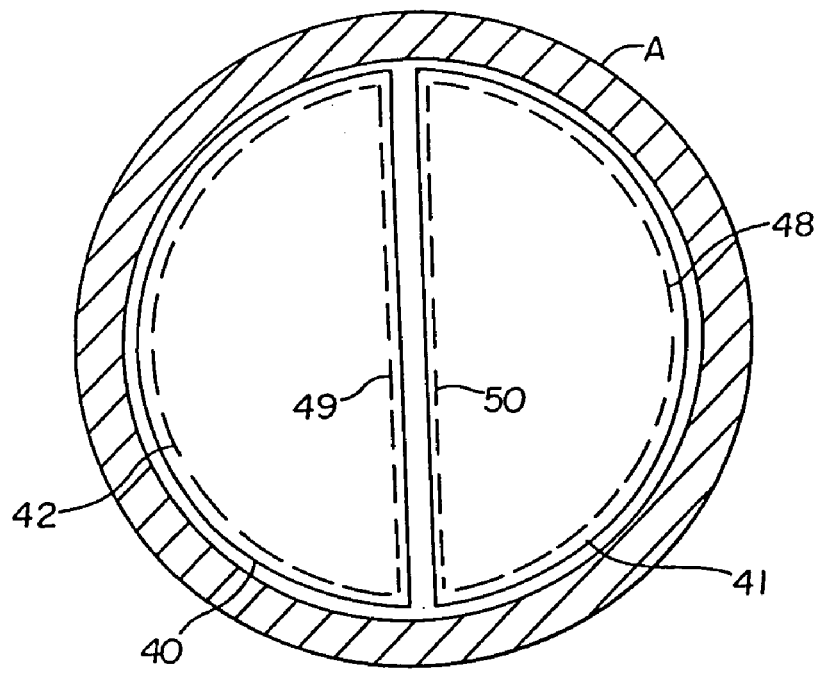
FIG. 4 is a cross-sectional view taken along line 4—4 of FIG. 3 showing the graft system positioned in the aorta, just below the renal arteries.

FIG. 4 is a cross-section taken along line 4—4 of FIG. 3. The D-shaped portion 42 of aortic stent 5 of leg 20 is shown aligned with D stent 48 of leg 30. D-shaped portion 42 aligns with D stent 48 along alignment surfaces 49 and 50. D-shaped portion 42 is surrounded by graft material 40 and D stent 48 is surrounded by graft material 41, forming a seal between legs 20 and 30 and the aorta.

The generally circular shape formed by the two "D" shapes of the stents serve to seal off the aneurysm from blood flow, thus directing all blood flow into the two lumens of the grafts. For an infrarenal aneurysm, the upper end of the graft 40 of each leg may be positioned as close as possible to the lowest renal artery, as depicted in FIG. 2. This maximizes the overlap between graft material and upper aortic neck, assuring a good seal within the artery.

Configuration of Legs of Graft System

Figure 5C:
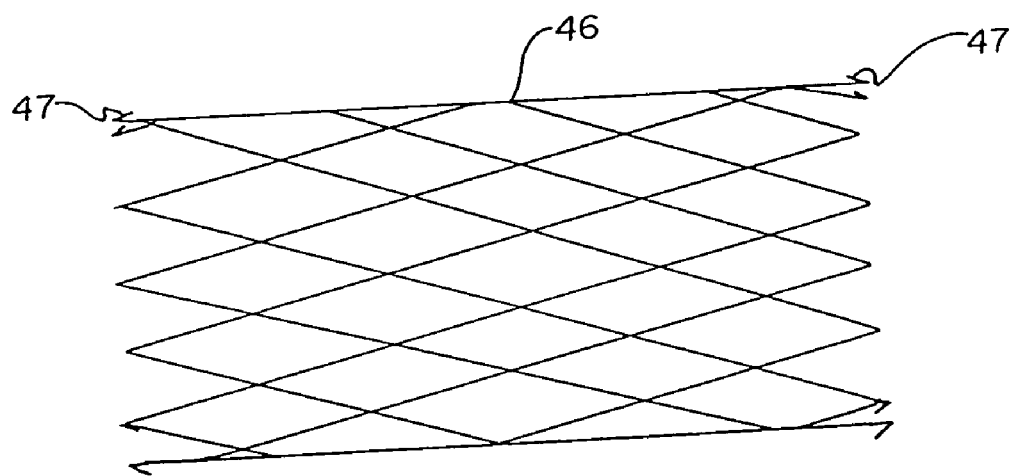
FIG. 5c is a plan view of a gripping stent.
Figure 5A:
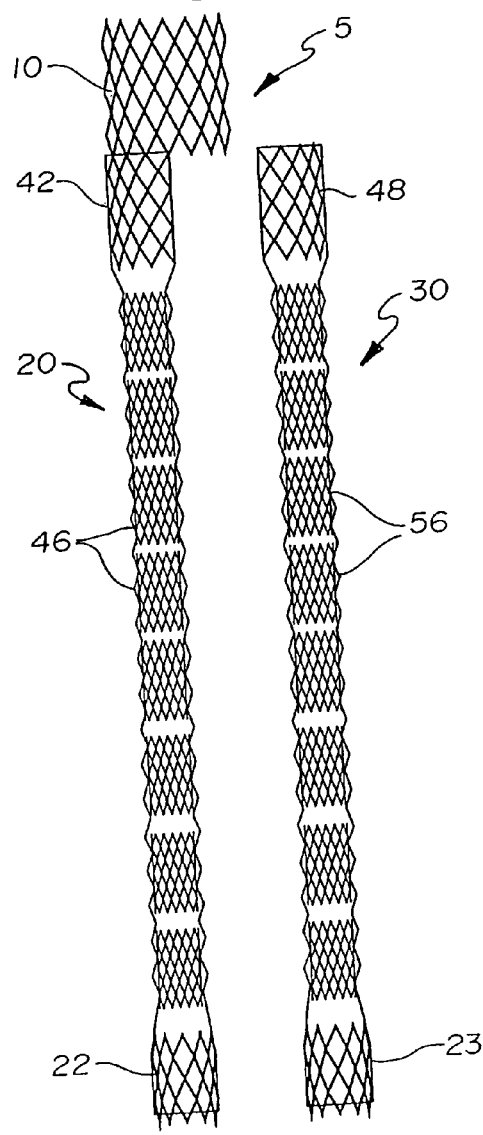
FIGS. 5a and 5b are views of the legs of the embodiment of FIG. 2 in extended and compressed form, respectively, with gripping stents in place showing the fully deployed shape of the graft system within the aneurysm.
Figure 5B:
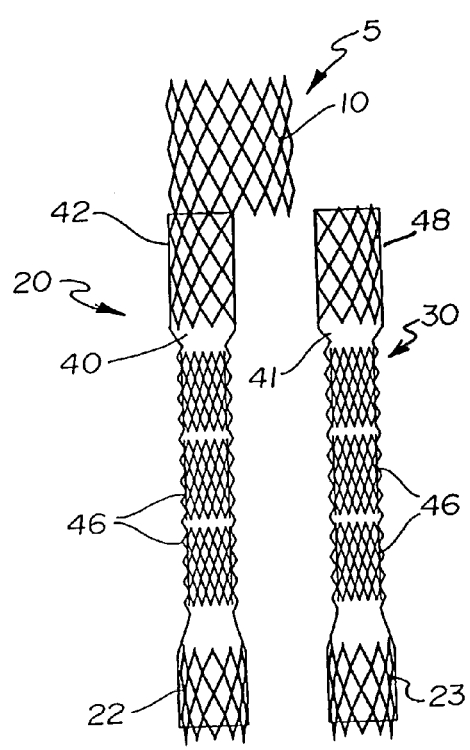

The overall configuration of legs 20 and 30 of the embodiment of FIG. 2 of the graft system can be best understood with respect to FIGS. 5a and 5b where the graft components are shown in section to better illustrate the configuration of the stent structure. FIG. 5a shows legs 20 and 30 in a more expanded configuration while FIG. 5b shows the legs in a less expanded configuration. Either of these configurations or modifications thereof could be used depending on the anatomy of the patient.

Leg 20 includes aortic stent 5 (D-O stent) with O-shaped portion 10 and D-shaped portion 42. D-shaped portion 42 is surrounded by graft component 40 which is fixed to the stent, preferably by sutures. The graft material which covers D-shaped portion 42 forms a D-shaped lumen. As the graft component 40 extends away from (below) D-shaped portion 42 the graft material tapers inwardly from the aortic region to a mid region or bellows region of graft component 40. The mid region of graft component 40 has a substantially circular cross-section, the diameter of which is preferably uniform. Near the caudal end of the leg the diameter preferably increases along another transition region to an iliac region of the graft component which is fixed over the iliac stent 22, preferably by sutures.

One or more gripping stents 46 are positioned between the aortic stent 5 and iliac stent 22 to secure the bellows region of the graft component in place after the length of the leg has been properly adjusted as will be discussed in more detail hereafter.

The location and configuration of the components of leg 30 are similar to that discussed with respect to leg 20. Specifically, aortic stent 48 is affixed to graft component 41, preferably by sutures. A series of gripping stents 56 is located in a mid region between aortic stent 48 and iliac stent 23.

Graft Component

Graft components 40 and 41 of legs 20 and 30 may be made of materials which include woven and knitted materials comprising polyester, polytetrafluoroethylene (PTFE), silicones, and urethanes. The materials may be porous or nonporous and may be opaque to X-rays. Preferred materials include polyester fabric, for example DACRON®, TEFLON®, or other suitable fabric.

A preferred fabric for use in the graft component is a 40 denier polyester yarn, having 180 to 250 end yarns per inch per face and 80 to 120 pick yarns per inch per face. At this weave density, the graft component is relatively impermeable to blood flow through the wall, but yet is relatively thin, ranging between 0.08 and 0.12 mm wall thickness. Preferably, the grafts are woven as tubes with appropriate tapers formed directly on the loom. However, desired dimensions for different regions of the graft component can also be achieved with suture lines or stitching of a flat fabric, or stitching a tubular fabric of an initial uniform perimeter equal to the desired perimeter of the aortic portion.

The graft component of each leg has a generally tubular shape. In a first embodiment shown in FIGS. 2 and 3, at least a portion of the graft component has a bellows mid region. The bellows or mid region is capable of extending and compressing longitudinally in response to any movement of the ends of the graft component. In a second embodiment discussed in connection with FIGS. 10–14 the bellows are focused more closely to the aortic portion of the graft component. In a third embodiment discussed later with respect to FIGS. 14–19 the graft component of each leg comprises at least two tubular overlapping or telescoping segments. One segment's diameter may be slightly larger than the other, such that a sealing fit is obtained in the overlapping region. All of these embodiments result in a graft system that allows the physician to adjust the length of the graft system in situ during the procedure.

In the first and second embodiments the bellows region is formed by placing the graft component in the fully elongate configuration on a mandrel containing a spiral shaped groove. A malleable wire, (e.g., copper) is wound around the graft, forcing the graft material to conform to the groove in the mandrel. The grooves are smaller than the graft material. The graft material is heat-set in an oven below the melting temperature of the graft material. Once removed from the mandrel, the bellows are set allowing the length of the graft component to be longitudinally adjustable during deployment by the physician by adjusting the position of the iliac region of the graft component. For example, a polyester graft component with heat set bellows over the full mid region of the graft component (approximately 12 cm) can elongate from about 11 cm in the fully compressed condition to about 20 cm in the fully elongated condition. For simplicity of depiction of the bellows, the graft components shown in, for example, FIGS. 5a and 5b show the full length of the middle region to have a bellows construction. However, only a portion of this region of the graft may have bellows.

The graft material of each graft component is attached to the aortic stent (the upper stent attachment region) and to the iliac stent (the lower stent attachment region) via sutures or other suitable attachment means. Attachment is typically, and preferably, done before the leg of the graft system is loaded into the delivery device.

In preferred embodiments, the graft is tapered below the upper stent attachment region. Such is illustrated in FIGS. 5a and 5b. For example, for an aneurysm neck of 28 mm diameter, the abutting portions of D stent 48 and D-shaped portion 42 would form a circle as shown in FIG. 4 with a minimum 14 mm minor diameter and at least 28 mm major diameter. Preferably, the major diameter is sized at least about 2 mm larger than the diameter of the aneurysm neck in order to insure a proper fit with no leakage and to accommodate either miscalculations in the size of the aorta or changes in size of the aorta after the procedure. Over a transition region of about 1 cm, a graft of this dimension preferably tapers to a uniform diameter ranging from about 8 to about 12 mm in the mid region. The graft component then flares up to a uniform diameter of about 12 to 16 mm in the lower stent attachment region.

Stents

Numerous stents are employed in the various embodiments of this invention. These stents could be self-expanding or expandable via an internal expanding device such as a balloon. Preferably, the stents are self-expandable and are comprised of a shape memory alloy. Such an alloy can be deformed from an original, heat-stable configuration to a second, heat-unstable configuration. The application of a desired temperature causes the alloy to revert to an original heat-stable configuration. A particularly preferred shape memory alloy for this application is binary nickel titanium alloy comprising 55.8% Ni by weight. This NiTi alloy undergoes a phase transformation at physiological temperatures. A stent made of this material is deformable when chilled. Thus, at low temperatures (e.g., below 20° C.), the stent is compressed so it can be delivered to the desired location. The stent is kept at low temperatures by circulating chilled saline solution. The stent expands when the chilled saline is removed and it is exposed to higher temperatures, e.g., 37° C.

Preferably, the stent is fabricated from a single piece of alloy tubing. The tubing is laser cut, shape-set by placing the tubing on a mandrel, heat-set to its desired expanded shape and size (e.g., D-O shape or D-shape) and electropolished. Electropolishing smoothes the surface of the alloy, which is believed to improve fatigue properties as well as extend the strain-to-fracture and also improves thrombogenicity resistance. Preferably, the shape setting is performed at 550° C. for approximately 20 minutes, followed by aging at 470° C. for 10 minutes. This heat treatment process provides for a stent that has a martensite to austenite transformation temperature range of less than 15 Celsius degrees, and an austenite finish temperature ($A_f$) of slightly less than 37° C.

Aortic Stent

As previously discussed, each leg 20 and 30 of the graft system includes an aortic stent. The aortic stents are shown in detail in FIGS. 6a–6d. Although discussed in particular with respect to legs 20 and 30 of the first embodiment the aortic stents of the other embodiments are similar and this discussion is applicable to those embodiments as well.

Stent 5 of leg 20 consists of an upper O-shaped portion 10 and a lower D-shaped portion 42. This stent consisting of the upper and lower portion is also referred to as the D-O stent. Stent 5 includes struts 43, shown in FIG. 6a, which are used to attach the "D"-shaped portion 42 of the stent to the "O"-shaped portion 10. It is preferred that only a few struts are used to effect the attachment, rather than every possible strut, as this facilitates uniform expansion of the upper circular portion of the D-O stent during deployment. For example, only the two struts at opposite ends of the alignment surface 49 (FIG. 4) may be attached.

Figure 6A:
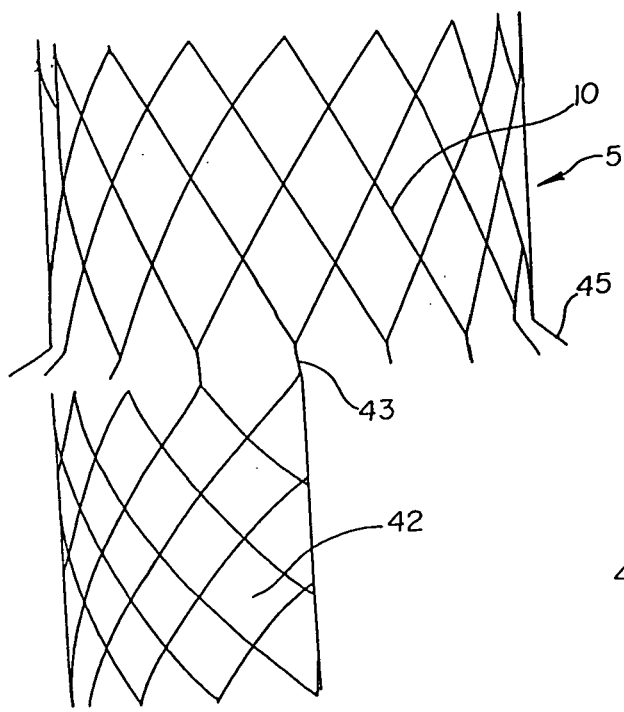
FIGS. 6a and 6b are a side view and a top view, respectively, of the D-O stent which comprises the aortic stent of one leg of the embodiment of FIG. 2.
Figure 6C:
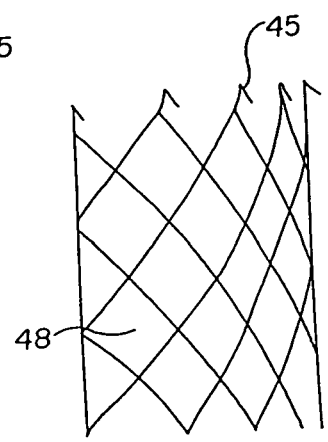
FIGS. 6c and 6d are a side view and a top view, respectively, of the D stent which comprises the aortic stent of a second leg of the embodiment of FIG. 2.
Figure 6B:
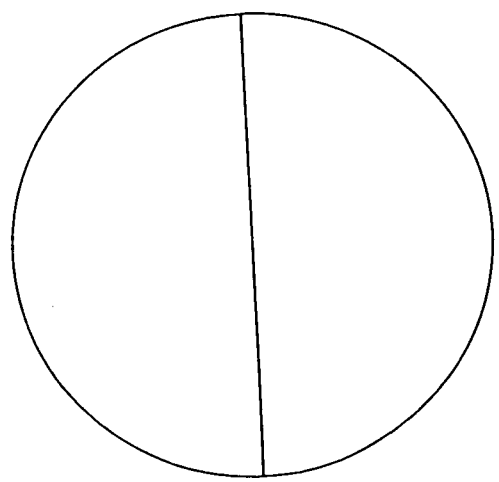
Figure 6D:
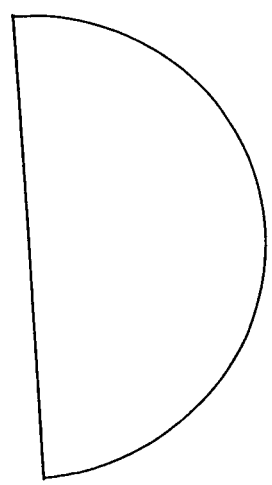

Upper portion 10 of the aortic stent is sized to fit the aorta. For example, for a 28 mm aorta, the stent diameter should be about 30 mm. Upper portion 10 is approximately 2 cm in length. It typically is desirable to "oversize" the stent to assure a good seal and engagement within the aorta. A minimum of about 2 mm oversize is preferred. Upper portion 10 is exposed, providing frictional engagement with the aorta. It is also expected that tissue ingrowth occurs faster with an exposed stent, leading to long-term anchoring of the stent. Barbs 45, hooks, or the like may be used to increase the mechanical fixation of the stent to the aorta. If barbs 45 are used, they are preferably placed at the lower end of the o portion of the stent, as shown in FIG. 6a. Alternatively, the barbs could be located in the D-shaped portion of the stent and project through the graft to engage the wall of the aorta.

The lower end of D-shaped portion 42 may have a taper to match the taper of the graft (from larger to smaller diameter sections of the graft in the bellows region).

D stent 48 of leg 30 is substantially D-shaped and has a configuration similar to the D-shaped portion 42 of D-O stent 5. This allows stent 48 to be aligned with lower portion 42 within the aorta as previously discussed in connection with FIG. 4. Stent 48 may be provided with barbs 46 which are provided to further secure the stent to the wall of the vessel, preventing caudal migration of leg 30.

Iliac stents

Iliac stents are attached at the lower end of the graft components, as shown in FIGS. 5a and 5b. Similar iliac stents are used in the other embodiments disclosed herein. Preferably, attachment is via sutures. The lower end (caudal) of the stent is positioned close to the internal iliac artery without covering the internal iliac artery with the stent. As the internal iliac is a significant vessel, it is desirable to avoid covering the ostium of the vessel with a stent or graft material.

Typically, the size of the iliac stents ranges from about 12 to about 16 mm. The stents may be oversized (i.e., larger than the estimated size of the iliac artery by about 2 mm). If they are oversized, excess graft material covering the stent is folded flat between the iliac stent and the iliac artery after deployment. This is also the case with excess graft material covering the aortic stents.

The iliac stent may also incorporate barbs, hooks, or the like (not shown) to further secure the iliac stent to the wall of the vessel.

Gripping Stents

Because the bellows region of the graft will tend to elongate when exposed to internal pressure (e.g., from blood pressure), maintenance of the proper length of the graft component is needed during deployment and in situ. Elongation of the bellows is minimized during deployment due to the presence of the internal delivery catheter and guide wire. These components tend to be stiff, preventing significant bowing and elongation of the bellows region, once the bellows have been compressed.

To prevent undesirable lengthening of the graft component once deployed, gripping stents 46 are deployed within the bellows region as seen in FIGS. 5a and 5b. These gripping stents, shown in FIG. 5c, prevent elongation of the bellows region due to friction between the graft material and the gripping stents which prevents migration or slipping of the graft material after the stent is deployed. Gripping stents 46 may be provided with barbs 47 at each end to further secure the shortened bellows region. One or more gripping stents may be used. It is important that the full length of the bellows region has gripping stents deployed within. In use, if the bellows region has been compressed to a relatively short length only a few gripping stents are necessary to cover the bellows region. If the patient's anatomy requires a longer leg length more gripping stents are required to fully cover the bellows region. These gripping stents are deployed immediately following the deployment of the iliac stent for each leg. Any small "snaking" of the bellows is eliminated once the gripping stents are deployed.

Delivery System and Method of Deployment

Bellows Embodiment

Figure 7:
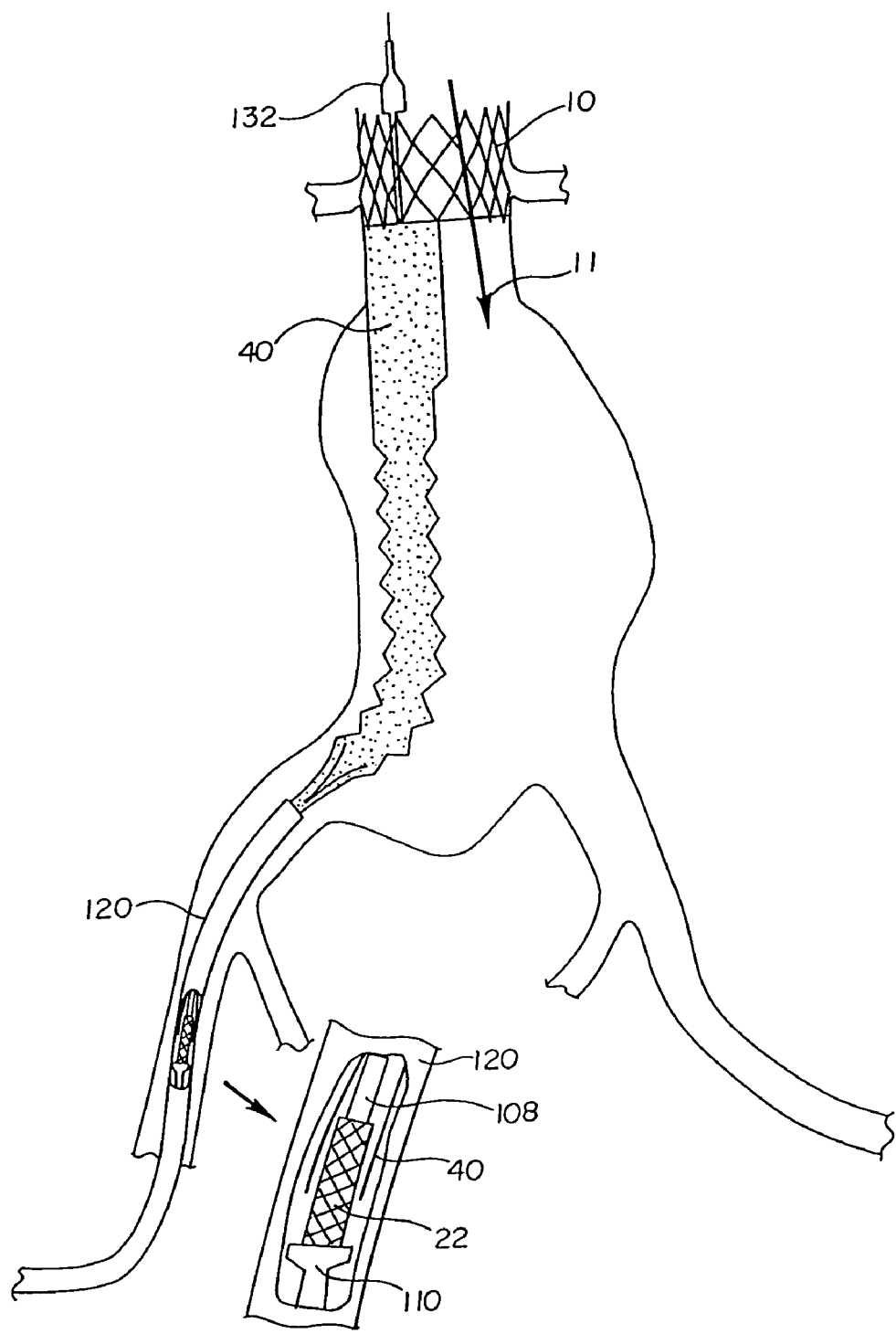
FIGS. 7, 8, 9a and 9b are diagrammatic views with portions partially cut-away and a portion exploded to show the method of delivery and deployment of one leg of the graft system of FIG. 2 on the right side of the aneurysm.
Figure 8:
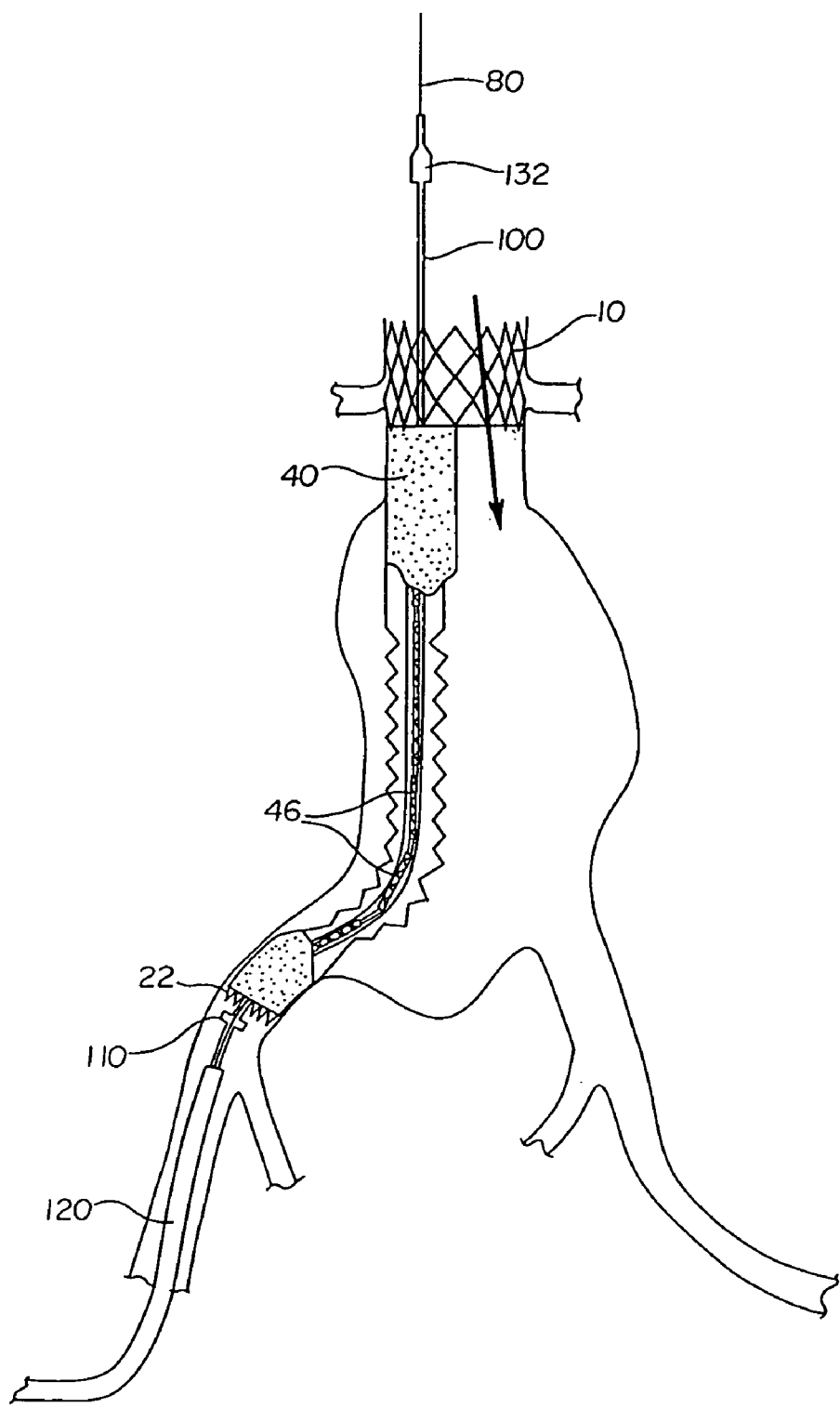
Figure 9A:
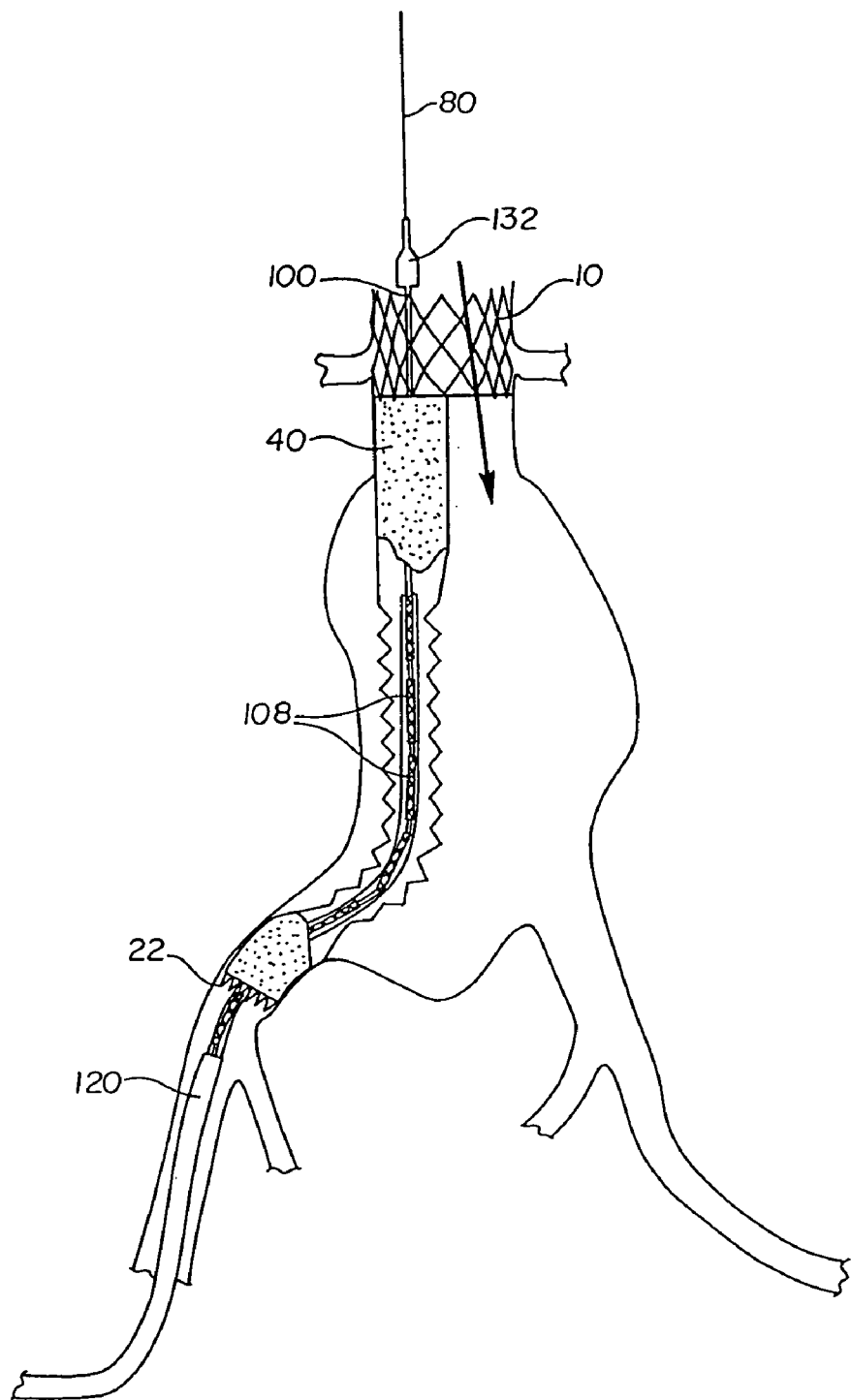
Figure 20:
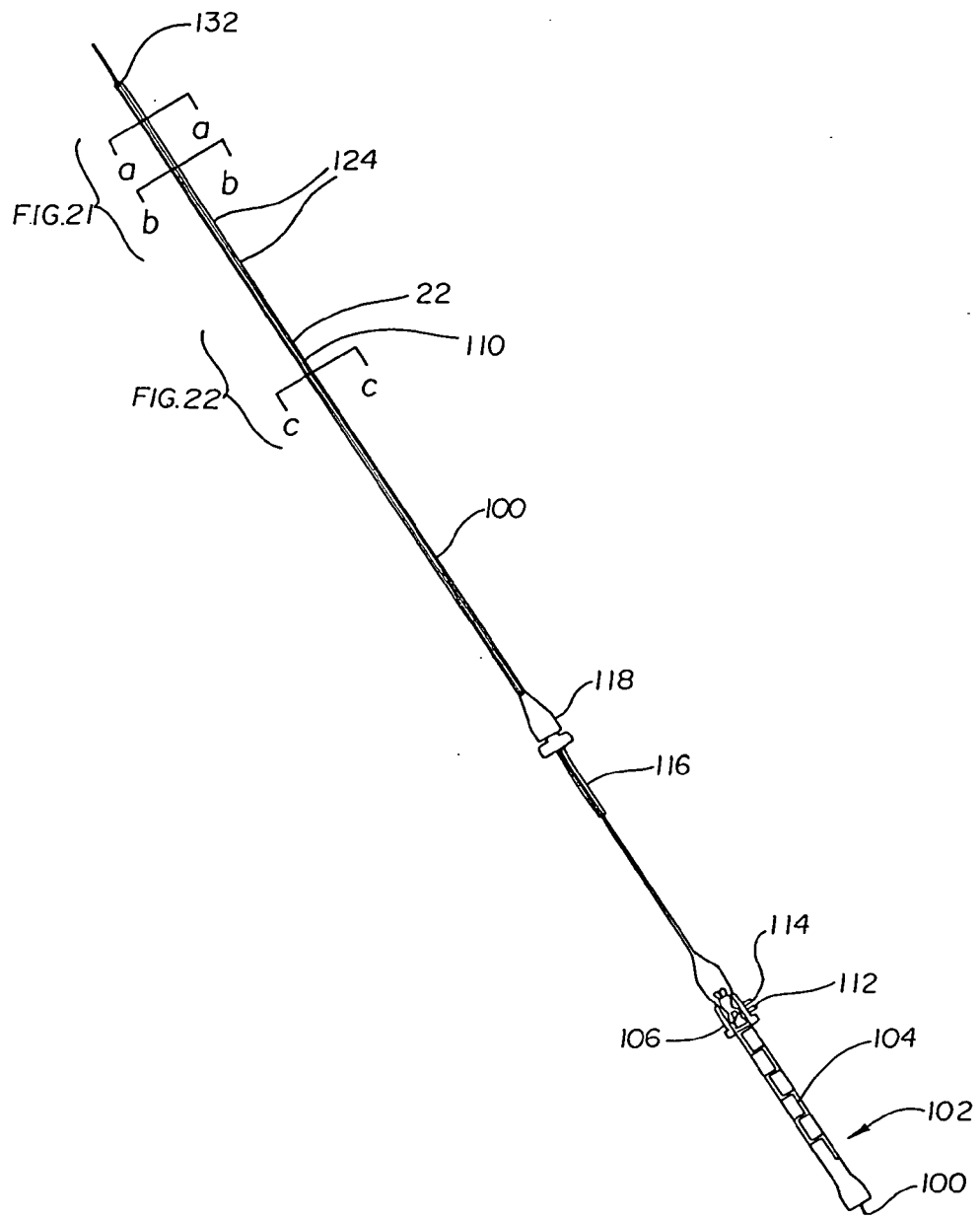
FIG. 20 is a cross-sectional view of the delivery system used to insert and deploy the graft system of the embodiment of FIG. 2.
Figure 20C:
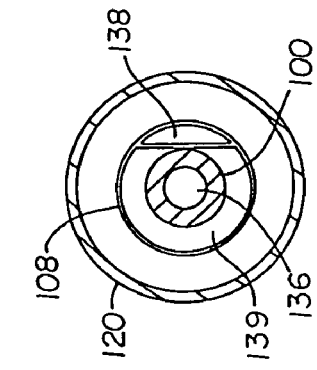
FIGS. 20a, 20b, and 20c are cross-sectional views taken along lines a—a, b—b, and c—c of FIG. 20, respectively.
Figure 20B:
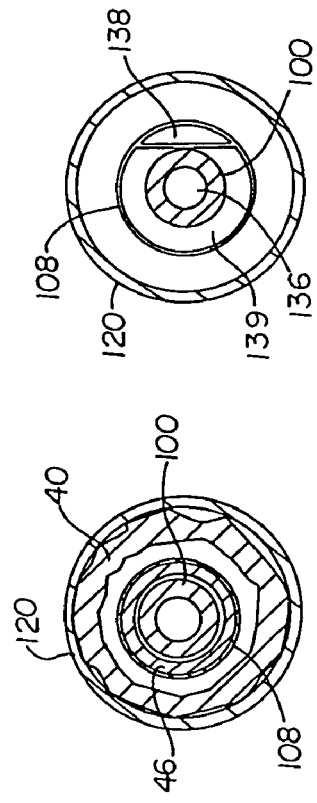
Figure 20A:
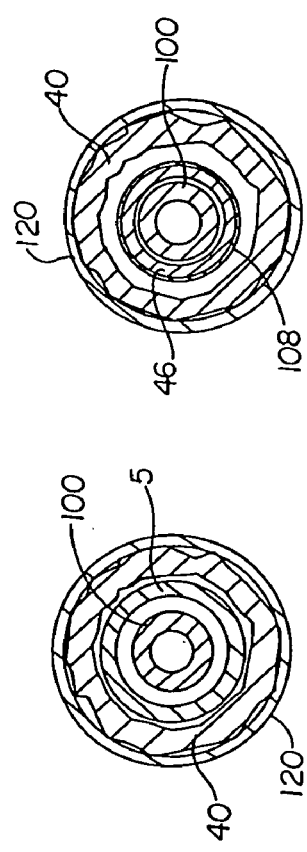
Figure 21:
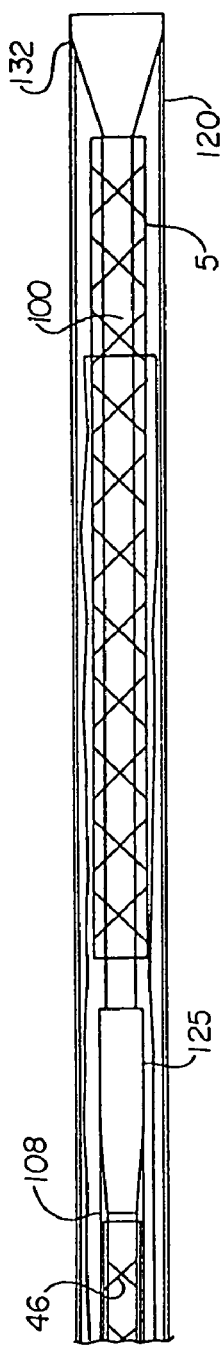
FIG. 21 is an enlarged cross-sectional view of a portion of the delivery device of FIG. 20.
Figure 22:
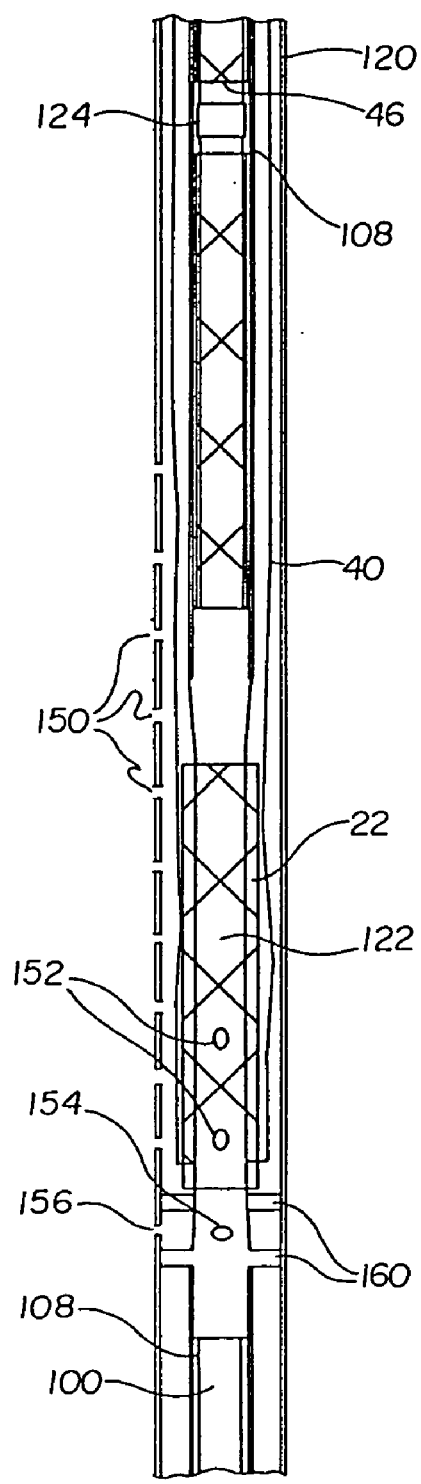
FIG. 22 is an enlarged cross-sectional view of a portion of the delivery device of FIG. 20.
Figure 23:
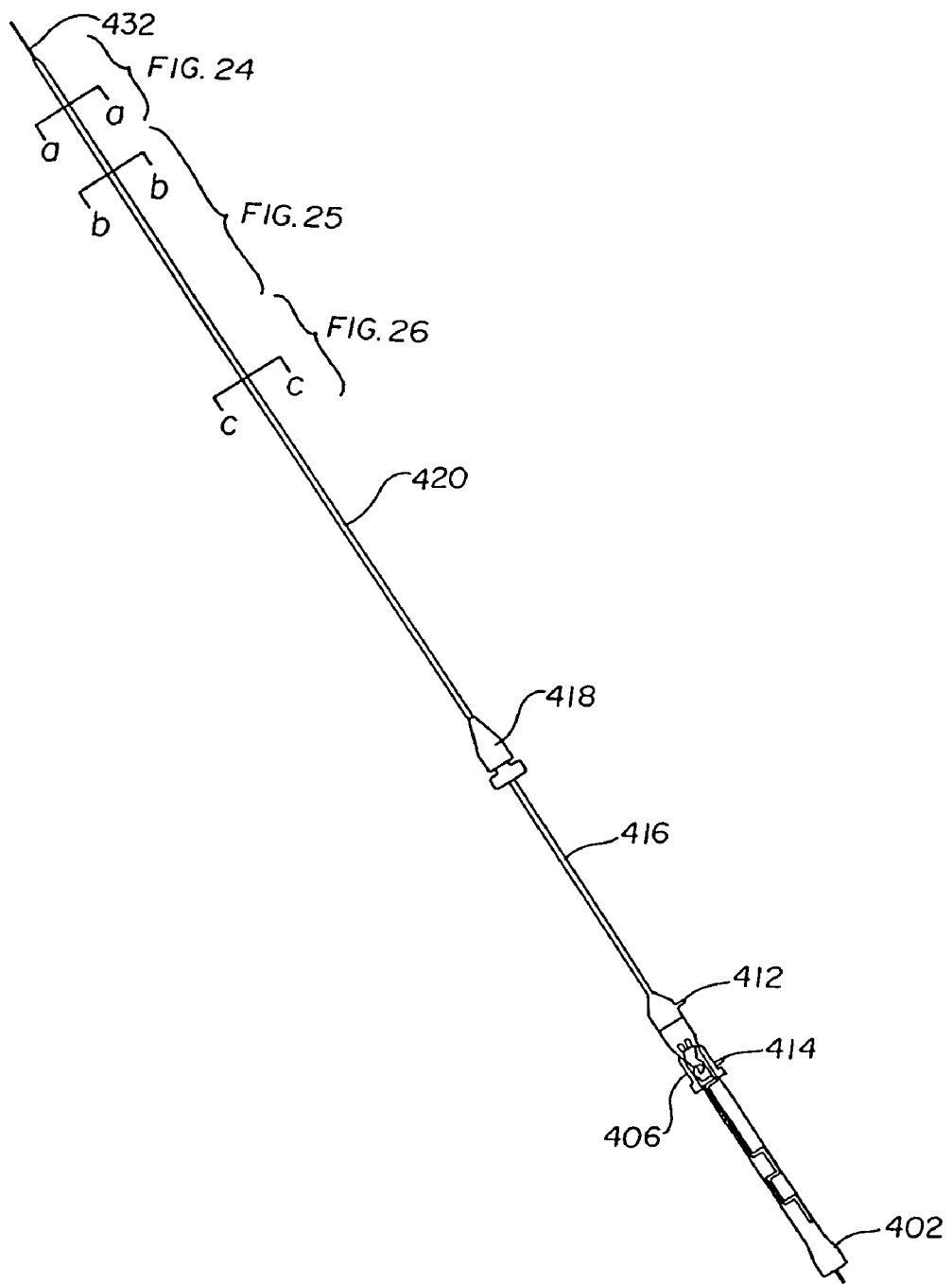
FIG. 23 is a cross-sectional view of the delivery system used to insert and deploy the graft system of the embodiment of FIG. 10.
Figure 23A:
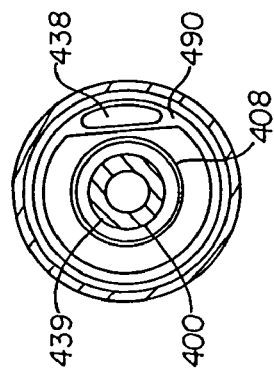
FIGS. 23a, 23b, and 23c are cross-sectional views taken along lines a—a, b—b, and c—c of FIG. 23.
Figure 23B:
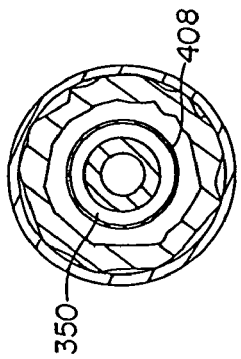
Figure 23C:
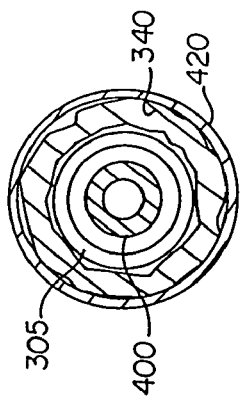
Figure 24:
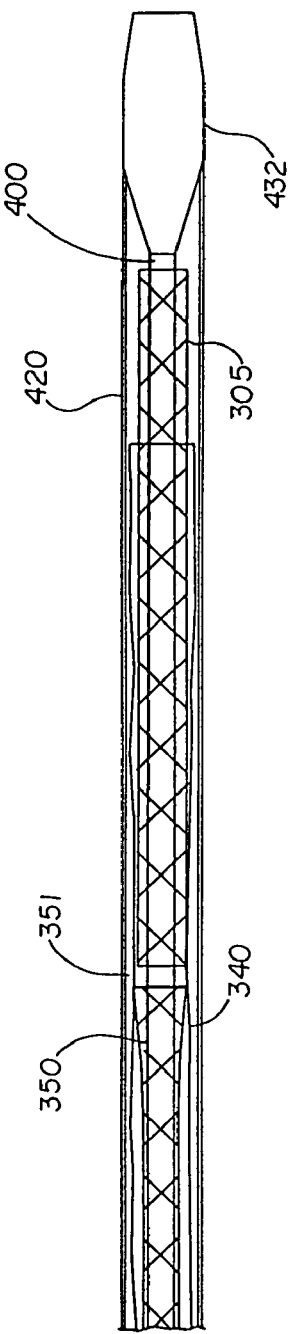
FIG. 24 is an enlarged cross-sectional view of a portion of the delivery system of FIG. 23.
Figure 25:
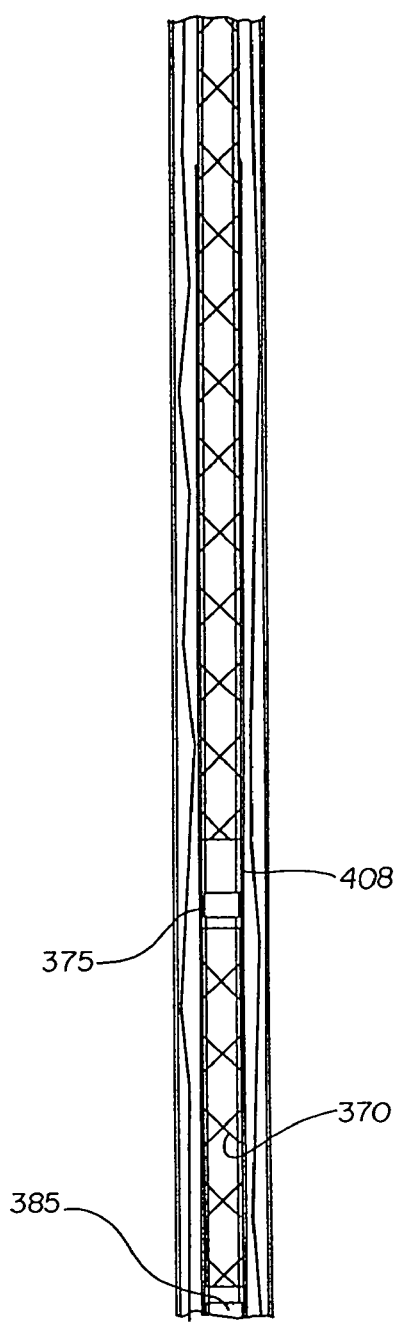
FIG. 25 is an enlarged cross-sectional view of a portion of the delivery system of FIG. 23.
Figure 26:
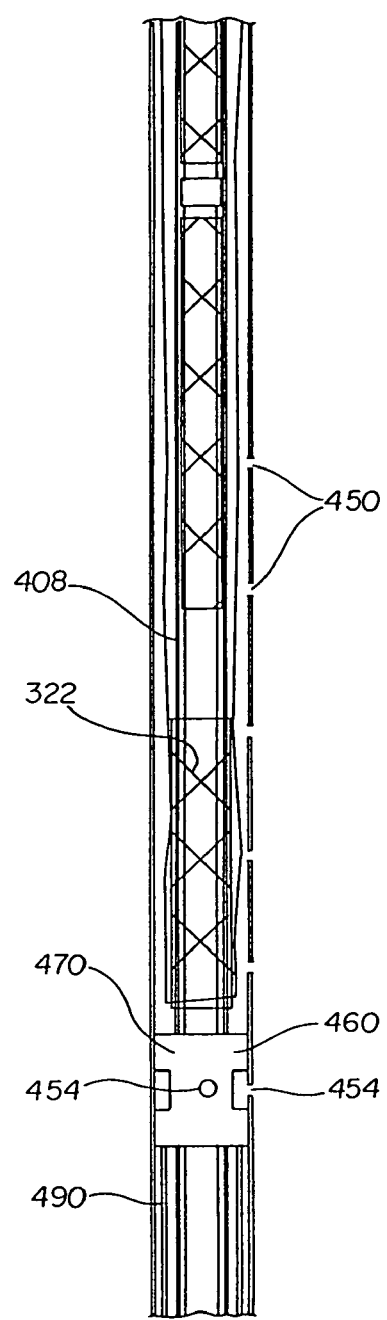
FIG. 26 is an enlarged cross-sectional view of a portion of the delivery system of FIG. 23.

Insertion of each leg of the graft system occurs via the delivery system shown in FIGS. 20–22. The manner in which the delivery system is used and the method of deploying the leg 20 of the graft system is illustrated in FIGS. 7–9. The femoral artery is entered within the thigh by an arterial incision where the vessel is close to the under-surface of the skin. A guide wire is first endoluminally placed, using conventional techniques to a position in the patient's thoracic aorta, above an aortic aneurysm such as depicted in FIG. 1. The delivery system of this invention is guided into the aneurysm along this guide wire. The guide wire remains in a fixed position throughout the endoluminal procedure. Conventional angiography techniques are employed to identify the aneurysm and the position of key anatomical structures such as the renal arteries.

The delivery system comprises main sheath 120, inner catheter 100, and gripping stent sheath 108. Main sheath 120 covers graft 40 and stents 22 (iliac) and 5 (aortic) in compressed configuration. Main sheath 120 preferably is formed of thin walled PTFE, having a thickness of approximately 0.003 to 0.010 inch, although other polymeric materials such as polyethylene or composite structures having a braid or coil may also be used. The main sheath diameter is in the range of about 12 to 18 French. Handle 102 is connected to inner catheter 100. Inner catheter 100 has a central lumen 136 capable of receiving a guide wire 80 (typically 0.035 to 0.038 inch diameter stainless steel). Inner catheter 100 has a distal end comprising solid bulb 132 which provides a gradual diameter transition between the guide wire and main sheath 120. A stiffness transition between the relatively flexible guide wire and the stiffer loaded main sheath 120 is provided by bulb 132 as well as by some length (e.g., 2 cm) of inner catheter projecting distally from bulb 132. This stiffness transition allows the loaded delivery system to be advanced through a tortuous path, often encountered in severe aneurysms. Inner catheter 100 runs through the full length of the delivery system. The aortic stent, the graft component, gripping stents and their sheath, and the iliac stent are mounted about the inner catheter.

Gripping stents 46 are covered by gripping stent sheath 108. At the proximal ends of the gripping stents are individual buttresses 124 which help maintain the position of the gripping stents when the gripping stent sheath is removed.

As best seen in FIG. 22, proximal of the most proximal gripping stent is a "land" area 122 on the gripping stent sheath. In this area the iliac stent 22 is positioned. Further proximal of the iliac stent, the gripping stent sheath becomes dual lumen, the first lumen 138 allowing for contrast delivery to facilitate location of the internal iliac artery and the second lumen 139 allowing for delivery of saline solution to cool the stents. The exit port 154 of the contrast lumen resides between two wiper seals 160, which transfer the contrast to one of a series of small holes 156 punched in the side of the main sheath. During delivery, the position of the main sheath relative to the gripping stent sheath and inner catheter will change and, therefore, more than one hole in the main sheath is required to assure that an exit is present for contrast imaging.

Handle 102 is located at the proximal end of the gripping stent sheath 108. Handle 102 is connected to inner catheter 100 and permits manipulation of inner catheter 100 and movement of the gripping stent sheath relative to the inner catheter. Handle 102 includes a sliding portion 106 connected to the gripping stent sheath. The path that the sliding portion takes is "zigzagged" to permit one gripping stent to be deployed at a time. Injection ports 112 and 114 are mounted on slider element 106. Through these ports are injected radiographic contrast solution and cold saline, respectively, which flow through the main sheath. The cold saline may exit from an orifice at the cranial end of main sheath 120, and/or from holes 150 in main sheath 120. The cold saline infusion keeps all of the stents cold until they are deployed. Holes 152 in the gripping sheath beneath the iliac stent keep the iliac stent chilled, and leakage distal to the distal end of the gripping stent sheath and into the distal end of the main sheath keep the gripping stents and the aortic stent chilled until they are deployed. The chilled saline keeps each of the stents in a martensitic phase, minimizing friction between the stents and sheaths for easier sheath retraction during deployment.

Aortic stent 5 and gripping stents 46 are mounted about inner catheter 100. Gripping stent sheath 108 holds gripping stents 46 and runs through the inside of iliac stent 22 when the system is packaged for delivery. At the distal end of gripping stent sheath 108 there is another buttress 125 mounted on inner catheter 100. It abuts gripping stent sheath 108 and acts to maintain the position of aortic stent 5 during its deployment.

At the proximal end of main sheath 120 is threaded swivel 118. Threaded swivel 118 engages with threads 116 on the outer surface of gripping stent sheath 108. Rotation of threaded swivel 118 controllably withdraws main sheath 120 relative to gripping stent sheath 108 and inner catheter 100 during deployment of the aortic stents. Careful controlled delivery of the aortic stent is important to assure its proper final location. This rotation on the threads provides this controlled withdrawal of the main sheath.

One leg of the graft system is positioned by advancing the delivery system over the guide wire, deploying the aortic stent, withdrawing the main sheath to expose all but the iliac stent, positioning the iliac stent, deploying the iliac stent, advancing the gripping stent delivery catheter, and deploying a sufficient number of gripping stents to fully stent the expanded section.

During deployment of the first leg of the graft system, the upper O-shaped portion 10 of the aortic stent serves to position "D"-shaped portion 42 to one side of the aorta, and makes room for the second leg to be positioned adjacent the first (i.e., the flat faces or alignment surfaces of the D-shape facing each other). O-shaped portion 10 also serves to anchor the first leg of the graft system to the aorta. To facilitate uniform expansion of the upper O-shaped circular portion of the D-O stent during deployment, it is desirable to limit the number of struts that are attached between the upper portion and the lower D-shaped portion. This is shown in greater detail in FIG. 6a, which shows struts 43 attaching the upper and lower regions of the stent on each side. Importantly, during deployment of either leg of the graft system, the aorta is never totally occluded. Therefore, there is never a stagnation pressure acting on the upper end of either leg during deployment. As seen in FIGS. 7–9, during deployment of leg 20, blood represented by arrow 11 can continue to freely flow within the aorta. This facilitates accurately positioning the aortic stents of both legs since no significant pressures are encountered which would tend to force the legs in a caudal direction during their deployment.

The deployment of leg 20 of the graft system is illustrated in FIGS. 7–9. The delivery system is advanced over the guide wire until the O-shaped portion 10 of aortic stent 5 is in proper position. Typically, the upper edge of the graft material is just below the lowest renal artery. Angiography is used to identify the renal arteries before deployment of the aortic stent. One or more radiopaque markers (not shown) positioned along the upper edge of the graft component are attached during manufacture. Additional radiopaque markers are placed along the upper edge of the alignment surfaces of the graft components attached to the D-shaped portion of aortic stent 5 and the D-stent to permit rotational alignment of the legs. To deploy aortic stent 5, inner catheter 100 and gripping stent sheath 108 are grasped via handle 102 and their positions maintained while main sheath 120 is withdrawn by turning threaded swivel 118 over threads 116 so that it moves in a proximal direction. Main sheath 120 is further withdrawn until the main sheath's distal tip is above iliac stent 122. This position is illustrated in FIG. 7, which shows the delivery of the aortic stent 5 at this stage. In FIG. 7, the iliac stent 22 is still at a point below the internal iliac branch.

The position of main sheath 120 is maintained while gripping sheath 108, gripping stents 46 and inner catheter 100 are advanced upwards, carrying iliac stent 22 and the iliac end of graft component 40 upward. Graft component 40 extrudes from the end of main sheath 120 causing the bellows in the mid region to compress. In order to properly position the iliac stent above the internal iliac artery, contrast lumen 138 is provided through gripping stent sheath 108. Holes are provided through the gripping stent sheath and the main sheath allowing the contrast fluid to exit the delivery device. When the contrast fluid is detected by the physician in the internal iliac branch the iliac stent 22 is in proper position. Main sheath 120 is further withdrawn, deploying iliac stent 22 and the lower edge of graft component 40. Part of gripping stent sheath 108, nearest iliac stent 22, serves as a buttress 110 to maintain the position of iliac stent 22 during withdrawal of main sheath 120. FIG. 8 illustrates the deployment of the graft-stent at this final stage of delivery. Inner catheter 100 and gripping stent sheath 108 are now moved up (i.e., in the cranial direction).

Leg 20 is now deployed. The bellows region has been compressed or extended as necessary to have the desired graft length. However, the bellows region will tend to elongate. The guide wire, gripping stent sheath 108, and inner catheter 100 will assist in maintaining the compressed shape of the bellows region during the deployment procedure. In order to permanently fix the shape of the graft component, gripping stents 46 are deployed. These are positioned beginning at the upper end of the bellows region. As gripping stents 46 have been advanced in the cranial direction due to advancement of the iliac stent to its proper position, the gripping stents typically need to be withdrawn to get to their proper position prior to deployment.

Figure 9B:
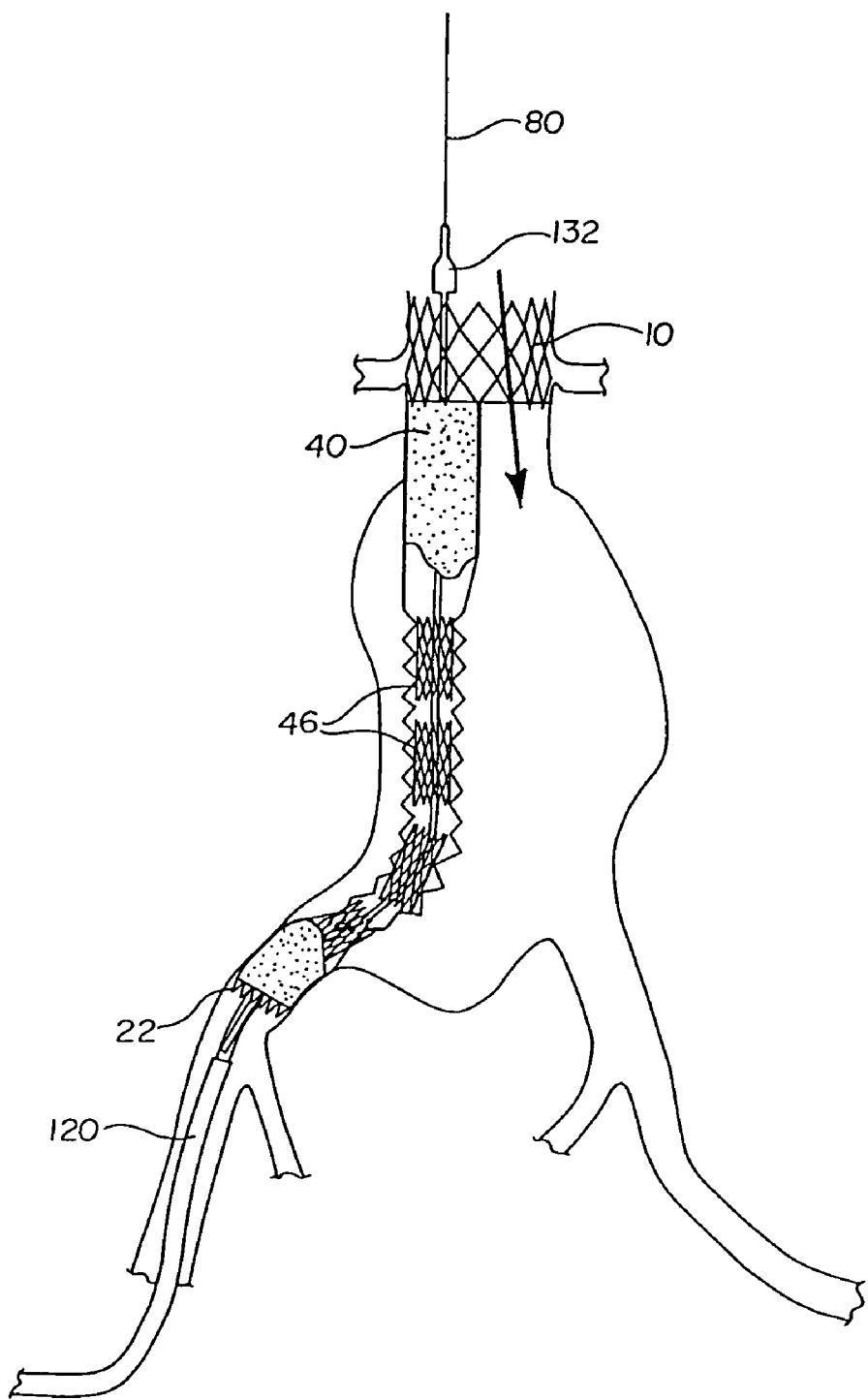

FIG. 9 illustrates the gripping stents and sheath after they have been moved caudally. Gripping stents are deployed in sequence by manipulating sliding portion 106 with respect to handle 102 thus forcing the graft component to take on a relatively straight shape. A sufficient number of gripping stents are deployed to align the graft component between the aortic and iliac stents. Extra gripping stents not needed are not deployed and are removed when the delivery device is removed. The gripping stents thus serve to straighten the bellows region of the graft, and to prevent them from further elongation after deployment of the system. Some space between adjacent gripping stents allows the graft to bend and accommodate any tortuosity within the vascular system. In this manner the gripping stents impart kink resistance to the graft. FIG. 9b shows the fully deployed gripping stents after gripping stent sheath 108 has been fully retracted.

Deployment of the second leg of the system is done in nearly the same manner as the first leg. The aortic stent 48 of leg 30 is identical to the lower D-shaped portion 42 of aortic stent 5 of leg 20. In deploying aortic stent 48, a radiopaque marker designating the flat face or alignment surface 50 (FIG. 4) of the stent is rotationally aligned with a similar marker on the alignment surface 49 of the D-shaped portion 42 of previously installed D-O stent 5. In this fashion, the flat faces of the adjacent aortic stents will properly face each other, assuring a proper orientation of both legs of the system, as illustrated in FIGS. 2, 3, and 4.

The second leg of the system is installed in the same manner as the first. This includes advancing the system over a pre-advanced guide wire, deploying the aortic stent, withdrawing the main sheath to expose all but the iliac stent, positioning the iliac stent, deploying the iliac stent, advancing the gripping stent delivery catheter, and deploying enough gripping stents to fully stent the bellowed portion of leg 30.

Focused Bellows Embodiment

Figure 10:
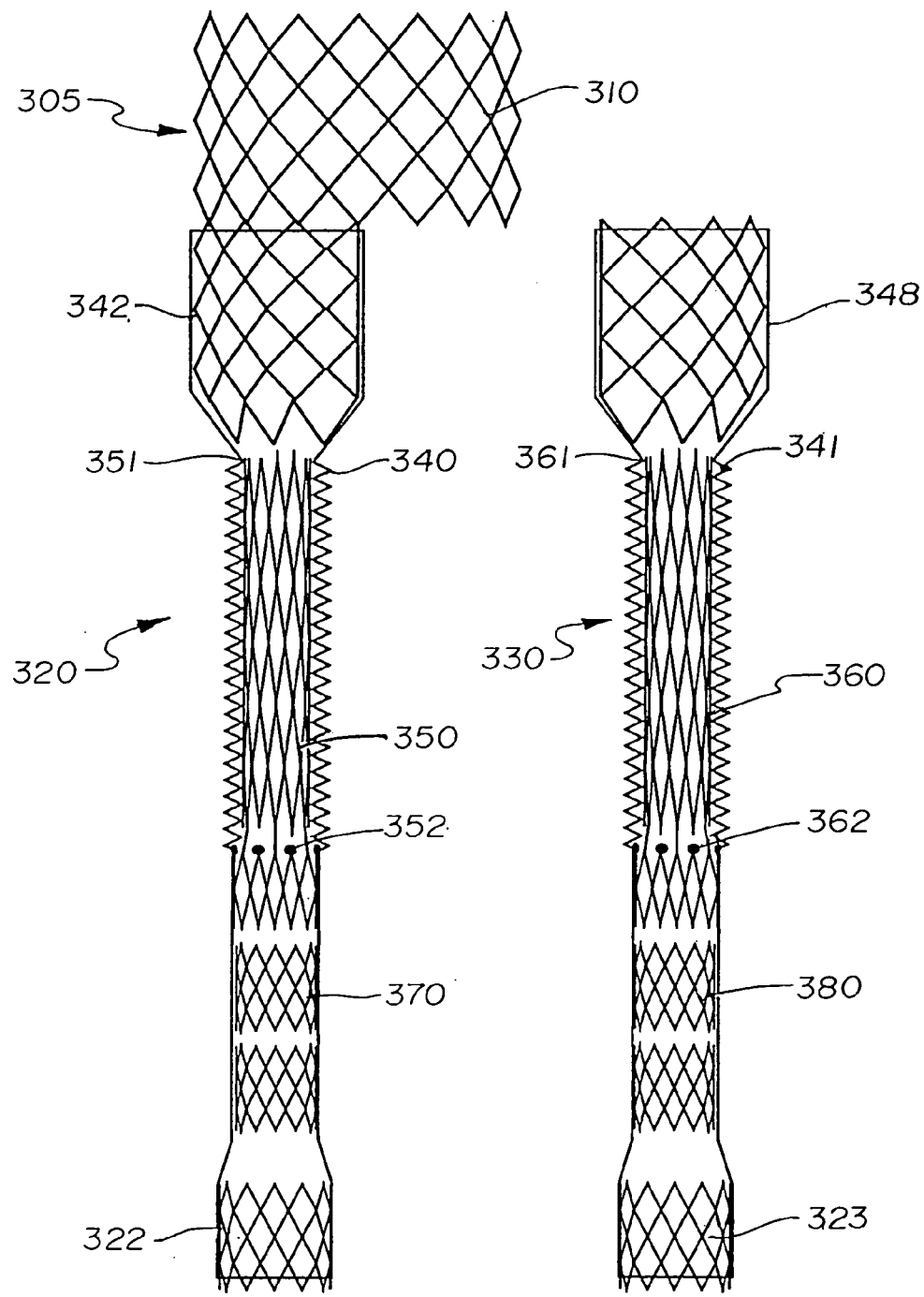
FIG. 10 is a plan view of the legs of a second embodiment of the graft system having a focused bellows configuration.

A second embodiment of the graft system which is a variation on the bellows concept previously discussed is disclosed in FIGS. 10–13. The structure of this embodiment is nearly the same as the first embodiment with the exception of the way the legs are stented in the mid region to achieve a concentration or focusing of the bellows at the upper portion of the mid region. With reference to FIG. 10 the graft system of this embodiment comprises two legs 320 and 330. Leg 320 includes aortic stent 305 having an O-shaped upper portion 310 and a D-shaped lower portion 342 which together define a D-O stent which is similar in configuration to aortic stent 5. Graft component 340 is attached to D-shaped portion 342, preferably by sutures.

Graft component 340 tapers from an aortic stent region surrounding D-shaped portion 342 down to a mid region having a generally circular cross-section. The sizes of the various components are similar to those discussed in connection with leg 20 of the bellows embodiment. Near the caudal or lower end of the graft component 340 the cross-sectional diameter increases along a transition area to an iliac stent attachment region which is affixed to iliac stent 322, preferably by sutures.

In the previous bellows embodiment, the graft component was bellowed along much of the length of the mid region and the subsequently deployed gripping stents fixed the as-adjusted length of the bellows region. Once deployed, the bellows of that embodiment are relatively uniformly spread out along the entire bellows region. In this embodiment, while the bellows are also formed along much of the length of the mid region of the graft component, any length adjustment necessary during deployment serves to "focus" or concentrate the bellows along the upper portion of the mid region nearest D-shaped portion 342. In both bellows concepts the bellows are fully stretched out when they are within the delivery system. This focused region is approximately 4 cm in length. When deployed the bellows that were formed in the remaining portion of the graft component remain fully extended or stretched out.

The concentrated or focused bellows are held in place by a special mid-stent 350 which is sutured at its upper end at points 351 to the graft material just below the transition from D-shaped portion 342. The mid-stent 350 is formed of a shape memory alloy as previously described. The lower portion of the stent may have multiple rearward facing prongs 352 (i.e., in a cranial direction) which are intended to engage the bellows and fix their position when the stent is deployed. Preferably, these prongs are smooth enough not to fray or puncture the graft material but are strong enough to engage the folds of the bellows to prevent the tendency to elongate caused by internal pressures in the graft.

Additional support stents 370 are provided between mid-stent 350 and iliac stent 322. These support stents provide radial support to prevent kinking or collapse of the graft component.

Leg 330 is similar to leg 320 except that aortic stent 348 is D-shaped to match with the configuration of D-shaped portion 342 of aortic stent 305 of leg 320. The relationship of aortic stents 305 and 348 is similar to that discussed with respect to aortic stents 5 and 48 of the bellows embodiment. Leg 330 further comprises a graft component 341, a mid-stent 360 sutured at points 361 to graft components 341 and having prongs 362, support stents 380 and an iliac stent 323, all of which are similar to their corresponding components of leg 320.

The delivery system for this embodiment is similar to the delivery system for the bellows embodiment with some exceptions which will be discussed below. The delivery system is shown in FIGS. 23–26. The delivery system comprises main sheath 420, inner catheter 400, and mid-stent sheath 408. Mid-stent sheath 408 extends distally and terminates such that it covers only the lower or proximal portion of the mid-stent. Since in this embodiment, the mid-stent 350 is attached to the graft component 340 and its position must always stay fixed relative to aortic stent 305 and the upper end of the graft component, the catheter/delivery device component that moves the iliac stent into position must not move the mid-stent. For this reason, the iliac stent cannot be mounted about the mid-stent sheath. In this embodiment, the mid-stent sheath 408 runs beneath the iliac stent, but does not engage the iliac stent. Thus, the iliac stent can be moved axially along the mid-stent sleeve so that it can be positioned properly for deployment. A lumen 439 is formed between inner catheter 400 and mid-stent sheath 408. Lumen 439 provides a path for cold saline.

An iliac stent buttress sleeve 490 runs over the mid-stent sleeve 408 and abuts the lower end of iliac stent 322. During iliac stent positioning the iliac stent buttress sleeve is advanced cranially until the iliac stent is in proper position relative to the aneurysm and the internal iliac branch. The iliac stent buttress sleeve has a lumen, 438 which provides a path for contrast fluid. The contrast lumen exits through hole 454 of iliac stent buttress 470 and through holes 450 in the main sheath.

Handle 402 is connected to inner catheter 400. Inner catheter 400 has a central lumen 436 capable of receiving a guide wire. Inner catheter 100 has a distal end which provides a gradual diameter transition between the guide wire and main sheath 420. Solid bulb 432 forms the catheter tip. A stiffness transition between the relatively flexible guide wire and the stiffer main sheath 420 is provided by bulb 432 as well as by some length (e.g., 2 cm) of the inner catheter projecting distally from bulb 432. This stiffness transition allows for the loaded delivery system to be advanced through a tortuous path, often encountered in severe aneurysms.

Handle 402 permits manipulation of inner catheter 400 and movement of the mid-stent sheath relative to the inner catheter. Handle 402 includes a sliding portion 406 connected to the mid-stent sheath 408. The path that the sliding portion takes is "zigzagged" to permit one support stent 370 to be deployed at a time. Injection ports 412 and 414 are mounted on handle 402. Through these ports are injected radiographic contrast solution and cold saline, respectively, which flow through the main sheath. The solutions may exit from an orifice at the cranial end of main sheath 420 and/or from holes 450 in main sheath 420. The cold saline infusion keeps all of the stents cold until they are deployed. Hole 454 in iliac stent buttress 470 provides a path for a contrast solution over the iliac stent. The chilled saline keeps each of the stents in a martensitic phase, minimizing friction between the stents and sheaths for easier sheath retraction during deployment.

At the proximal end of main sheath 420 is threaded swivel 418. Threaded swivel 418 engages with threads 416 on the outer surface of mid-stent sheath 408. Rotation of threaded swivel 418 controllably withdraws main sheath 420 relative to mid-stent sheath 408 and inner catheter 400 during deployment of the aortic and iliac stent.

The first leg 320 of the system with the D-O stent 305 is delivered first, in a manner similar to the previous bellows embodiment. Conventional angiography is used to locate the renal arteries and the delivery system is advanced over a previously placed guide wire until the upper end of the leg 320 is in the desired position relative to the renal arteries. The main sheath is then withdrawn, allowing the D-stent to expand. As in the other embodiments, the O-shaped portion 310 of the aortic stent 5 may be placed across the renal arteries. If the upper neck of the aneurysm is long enough, the entire D-O stent can be positioned below the renal arteries.

Figure 11:
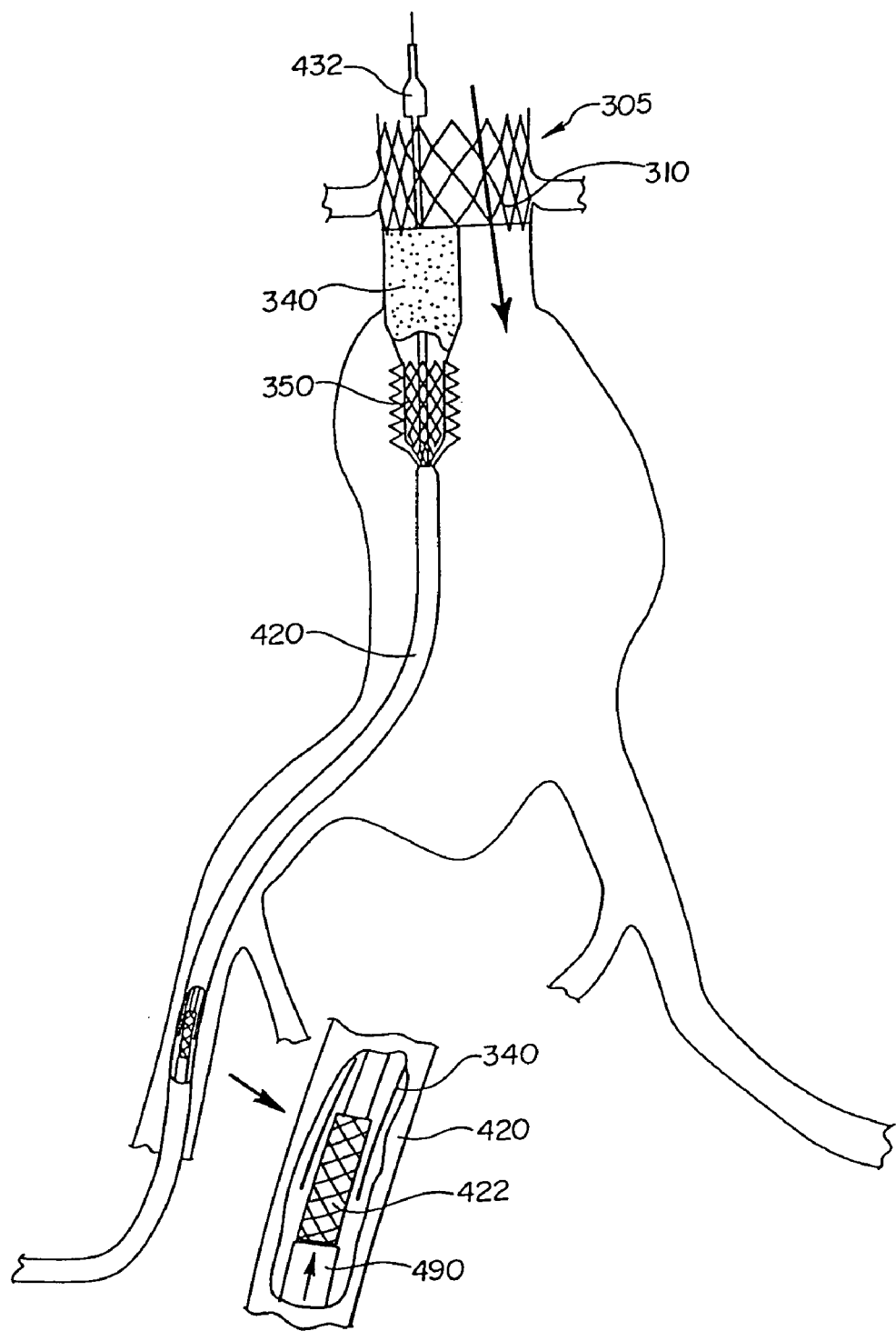
FIGS. 11–13 are diagrammatic views with portions partially cut-away and a portion exploded to show the method of delivery and deployment of one leg of the embodiment of FIG. 10.
Figure 12:
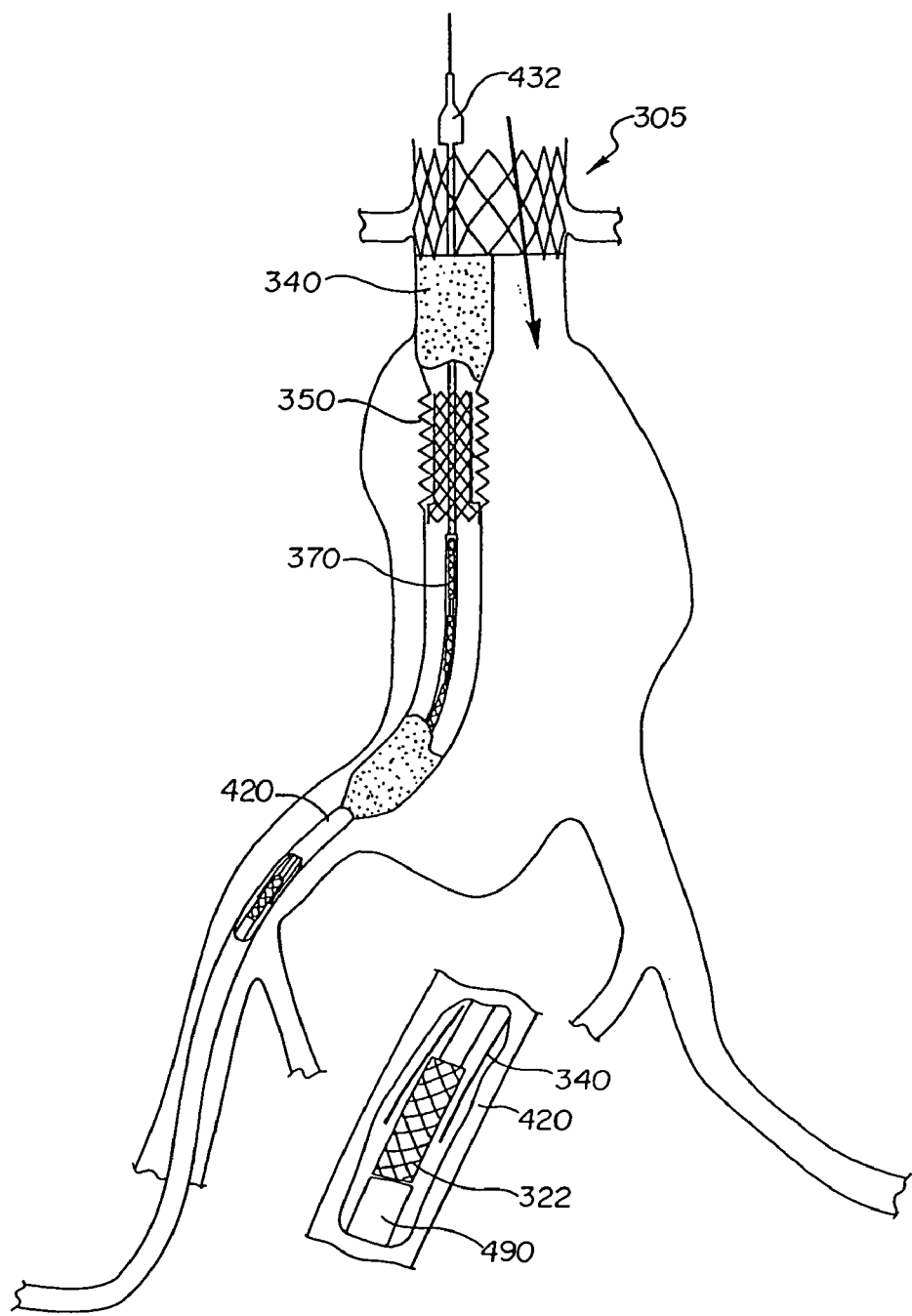
Figure 13:
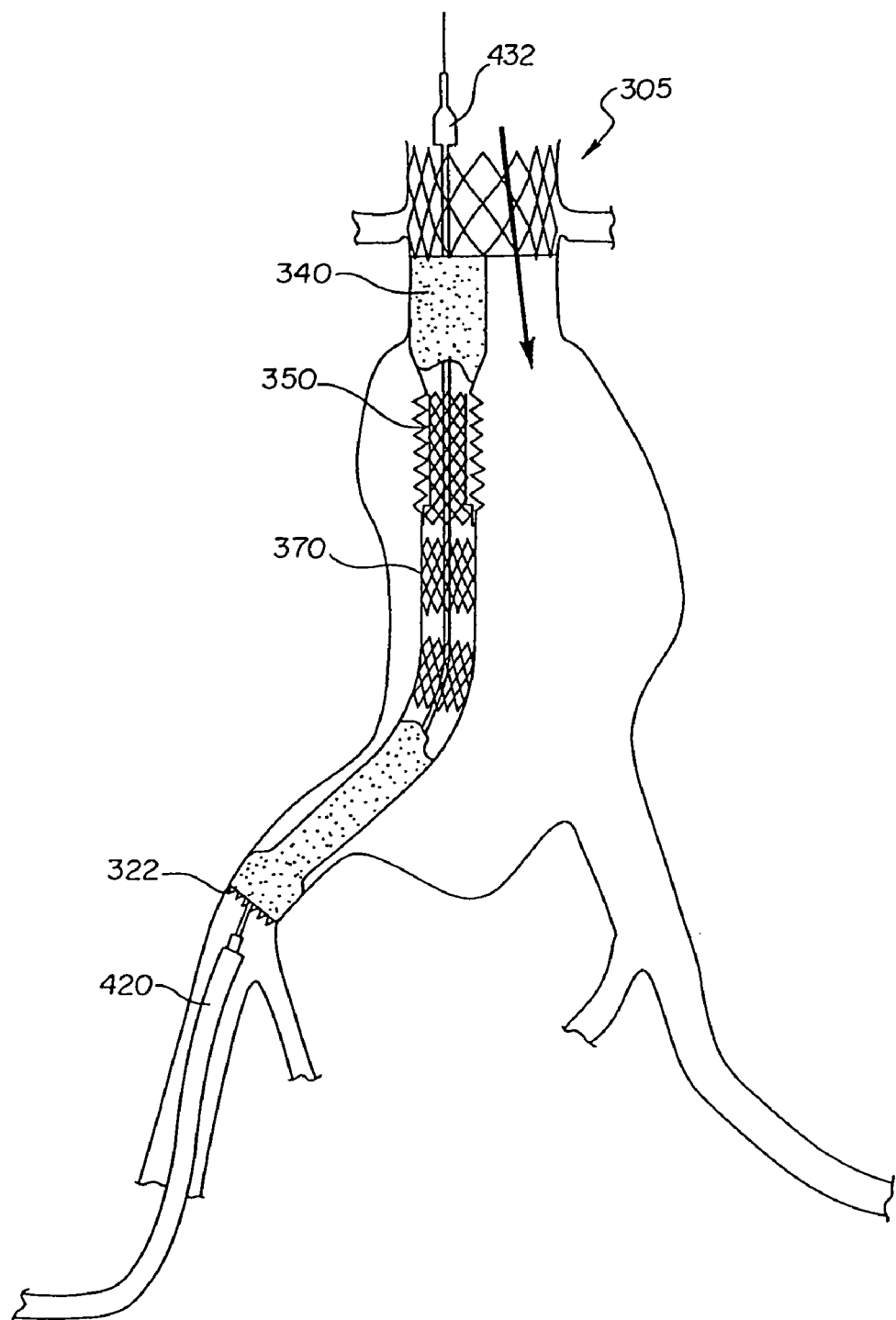

The method of delivery of the graft system can best be understood with reference to FIGS. 11–13. In FIG. 11 aortic stent 305 has been deployed in an appropriate position with O-shaped portion 310 located across the renal arteries. The main sheath 420 is withdrawn until the caudal end of the mid-stent 350 has been reached. At this position, a portion of mid-stent 350 has been expanded. At this point in the deployment procedure the iliac stent buttress sheath 490 is advanced cranially until the iliac stent 322 is in a desired position relative to the aneurysm and internal iliac branch (see insert of FIGS. 11 and 12). Contrast injection through the iliac stent buttress sheath facilitates this positioning. As the iliac stent is advanced, the bellows of the graft begin to stack-up over the mid-stent, once the bellows emerge from the distal end of the main sheath.

Once the iliac stent is in proper position, the mid-stent sheath 408 is retracted by manipulating sliding portion 406 of handle 402 to fully expand the rest of the mid-stent as best seen in FIG. 12. Once the mid-stent is fully expanded, the focused bellows are "locked in" by the expansion of the lower portion of the third stent and its barbs. Then the main sheath is withdrawn further until the iliac stent 322 is released (FIG. 13). Even though a portion of the graft component below the concentrated bellows region was previously formed with bellows, because the graft is loaded in the fully elongated or flattened state those bellows remains flattened since they did not exit the end of the main sheath during the stage when the bellows were being concentrated.

Once the iliac stent is expanded, the mid-stent sheath 408 is further withdrawn to allow a sufficient number of support stents 370 to expand in the remainder of the graft between the mid-stent and iliac stent. Any unused support stents are removed with the delivery device.

The second leg 330 of the system with D-shaped aortic stent 348 is deployed on the contralateral side in the same manner. Markers on or near the flat side of the D-stent are utilized to orient the D-stent to the D-shaped portion of aortic stent 305 of leg 320 assuring proper deployment and mating of the flat alignment surfaces of the upper ends of each leg. After that, the procedure for deploying the remainder of the stents is the same as described above with respect to leg 320.

Telescoping Leg Embodiment

A third embodiment allowing for in situ adjustment of the legs of the graft system is shown in FIGS. 14–19. In this embodiment each leg of the graft system has upper and lower graft segments which fit together telescopically to provide longitudinal length adjustment.

Figure 14A:
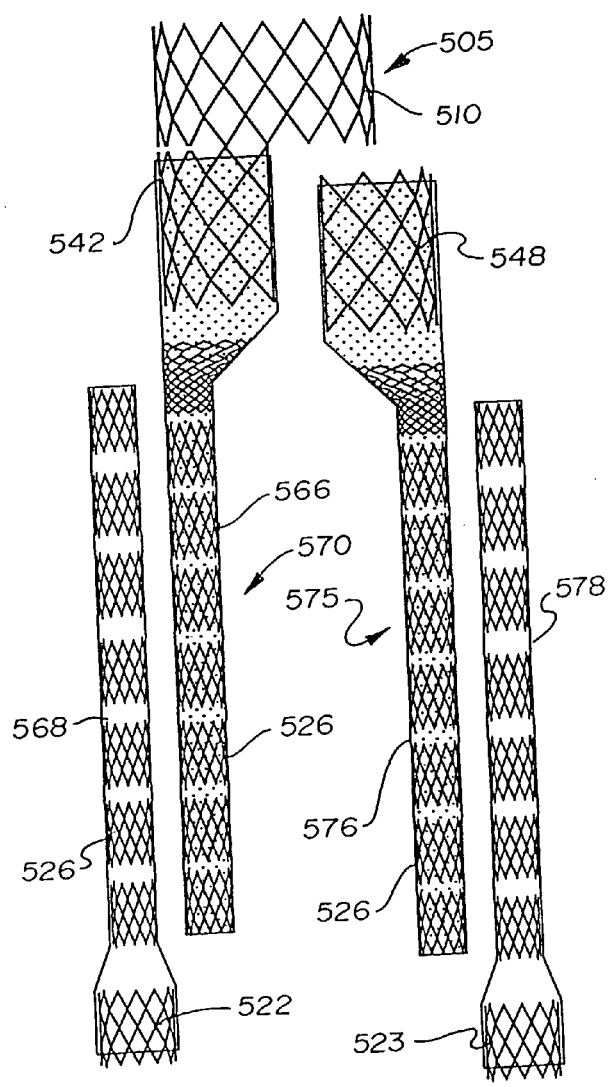
FIG. 14a illustrates a third embodiment of the adjustable length feature of the graft system showing upper and lower telescoping graft segments of each leg of the graft system with the graft component sectioned to illustrate the internal stent structure of this embodiment.
Figure 14B:
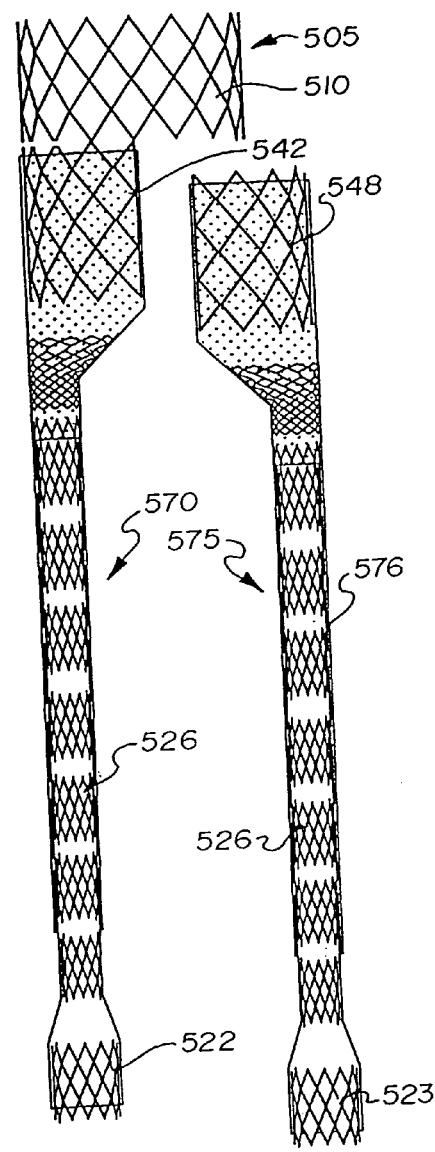
FIG. 14b shows the embodiment of FIG. 14a with the graft segments overlapped in a telescoping arrangement.

FIGS. 14a and 14b of the telescoping graft system having legs 570 and 575. Leg 570 comprises upper graft segment 566 and lower graft segment 568 and leg 575 comprises upper graft segment 576 and lower graft segment 578. The upper and lower graft segments of each leg are designed such that the lower graft segment fits within the upper graft segment in a telescoping arrangement. FIG. 14b illustrates the legs in their deployed and telescoping positions. The positions of the sections relative to one another are maintained by deployment of a plurality of support stents 526.

As best seen in FIGS. 14a and 14b, the upper graft segment includes a first aortic region surrounding the D-shaped portion of the aortic stent. This region may be approximately 2 cm long. The graft component then tapers down over a length of approximately 2 cm to a uniform diameter mid region. This mid region has a diameter of approximately 10 mm and a length of approximately 8.25 cm. The lower graft segment has a mid region of approximately 10 mm in diameter and 8.25 cm in length. The mid region then flares up from 10 mm to 16 mm over a transition length of approximately 0.5 cm. The lower graft segment contains an iliac region of approximately 16 mm in diameter which is approximately 1 cm long.

With this configuration, the minimum length of the two overlapped segments is 13.75 cm, which occurs when both segments' mid regions are fully overlapped. When the segments are installed in their longest configuration, approximately 2 cm of the mid regions should overlap yielding a total graft length of approximately 20 cm.

Although this embodiment is shown with two graft segments it will be appreciated that additional segments could be utilized to further extend the length of the telescoping graft.

Figure 28:
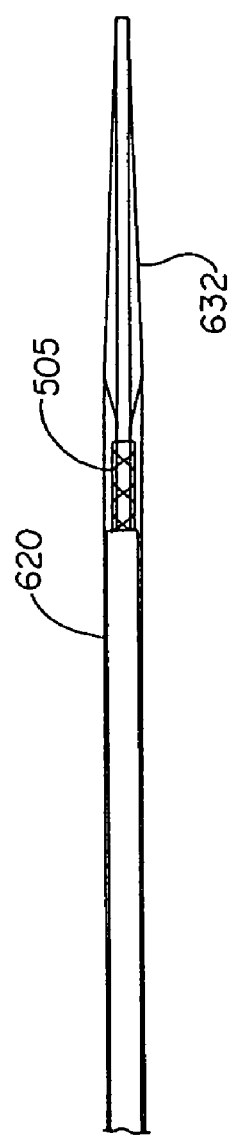
FIG. 28 is an enlarged cross-sectional view of a portion of the delivery system of FIG. 27.
Figure 29:
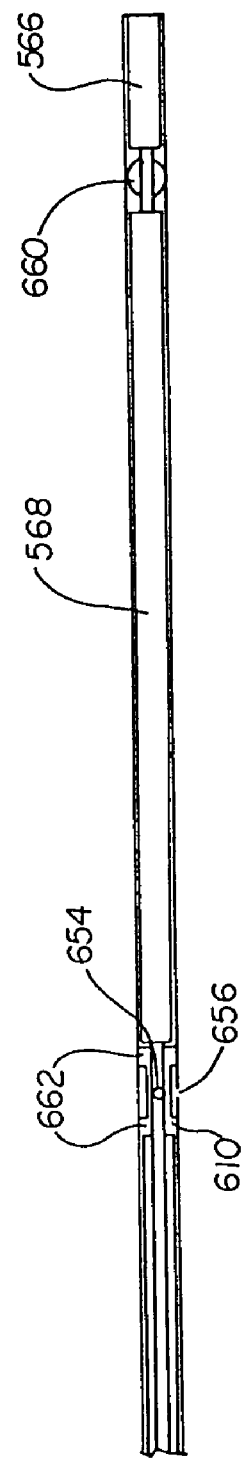
FIG. 29 is an enlarged cross-sectional view of a portion of the delivery system of FIG. 27.

The deployment of this graft system is accomplished via the delivery system shown in FIGS. 27–29. As in the previous embodiment, the delivery system comprises an inner catheter 600 which has a guide wire lumen suitable for passage of a 0.035 or 0.038 inch guide wire. Both the upper 566 and lower 568 segments of the legs are loaded into the delivery system around inner catheter 600. The upper graft segment is loaded near the aortic end (cranial) while the lower graft segment is loaded caudal or towards the iliac end of the delivery system. Preferably, these graft segments are loaded with no overlap between them. The main sheath 620 surrounds these graft segments.

At the distal end of the inner catheter is a flexible bulb 632 which serves the same purpose as discussed with respect to the other embodiments. An aortic stent buttress (not shown) is mounted on the inner catheter just proximal of the aortic stent. This buttress serves to keep the aortic stent in position as the main sheath is withdrawn during deployment. The inner catheter has a secondary bulb 660 located just proximal to the upper graft segment. This bulb serves as a smooth diameter transition region for the main sheath once the main sheath is completely removed from the upper graft segment. This allows for smooth advancement of the lower graft segment up into the upper graft segment once the upper graft segment has been expanded and deployed. The lower graft segment is positioned just proximal of the secondary bulb.

An iliac stent buttress 610 is mounted about the inner catheter just proximal of the iliac stent (not shown) which is sutured to the proximal end of the lower graft segment. The iliac stent buttress maintains the position of the iliac stent as the main sheath is withdrawn from the lower graft segment.

The inner catheter has a dual lumen proximal of the iliac stent buttress. The second lumen 639 provides a path for cold saline infusion. The first lumen 638 is used for contrast delivery to locate the internal iliac branch during iliac stent positioning as described in connection with the previous embodiments. Dual wiper or seal rings 662 surround the exit 654 of the contrast lumen to convey contrast from the inner catheter through a hole 656 positioned in the main sheath. In this embodiment, only a single hole is necessary, as the main sheath will be at a predetermined location relative to the inner catheter and contrast lumen at the time of iliac stent and lower graft segment positioning.

The inner catheter should be long enough proximal to the main sheath to allow for at least 20 cm of withdrawal of the main sheath. The main sheath of this delivery system is similar to those of the previous embodiments.

In this embodiment, the cold saline infusion is infused between the inner catheter and the main sheath, exiting at the distal end of the main sheath. This results in all stents being chilled prior to their release after withdrawal of the main sheath.

Figure 15:
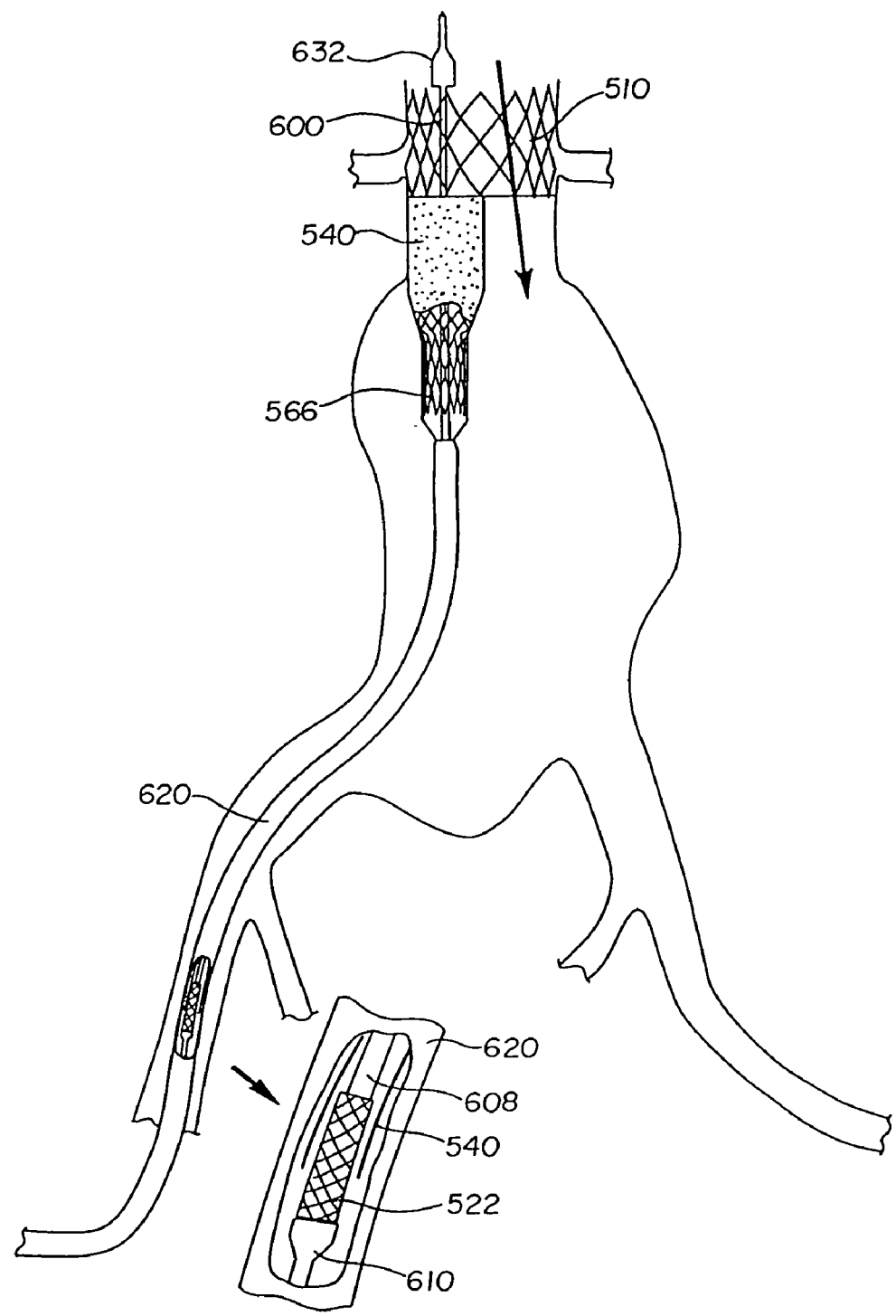
FIGS. 15–19 are diagrammatic views with portions partially cut-away and a portion exploded to show the method of delivery and deployment of one leg of the graft system of the embodiment of FIGS. 14a and 14b.

FIGS. 15–19 illustrate the deployment of the telescoping leg embodiment in the human vasculature. FIG. 15 illustrates the placement of the delivery catheter with distal bulb 632 at the cranial end of the aorta. O-shaped portion 510 is in position and the right leg of the graft system is in position. Main sheath 620 is partially retracted and graft component 540 is deploying into its expanded position.

Figure 16:
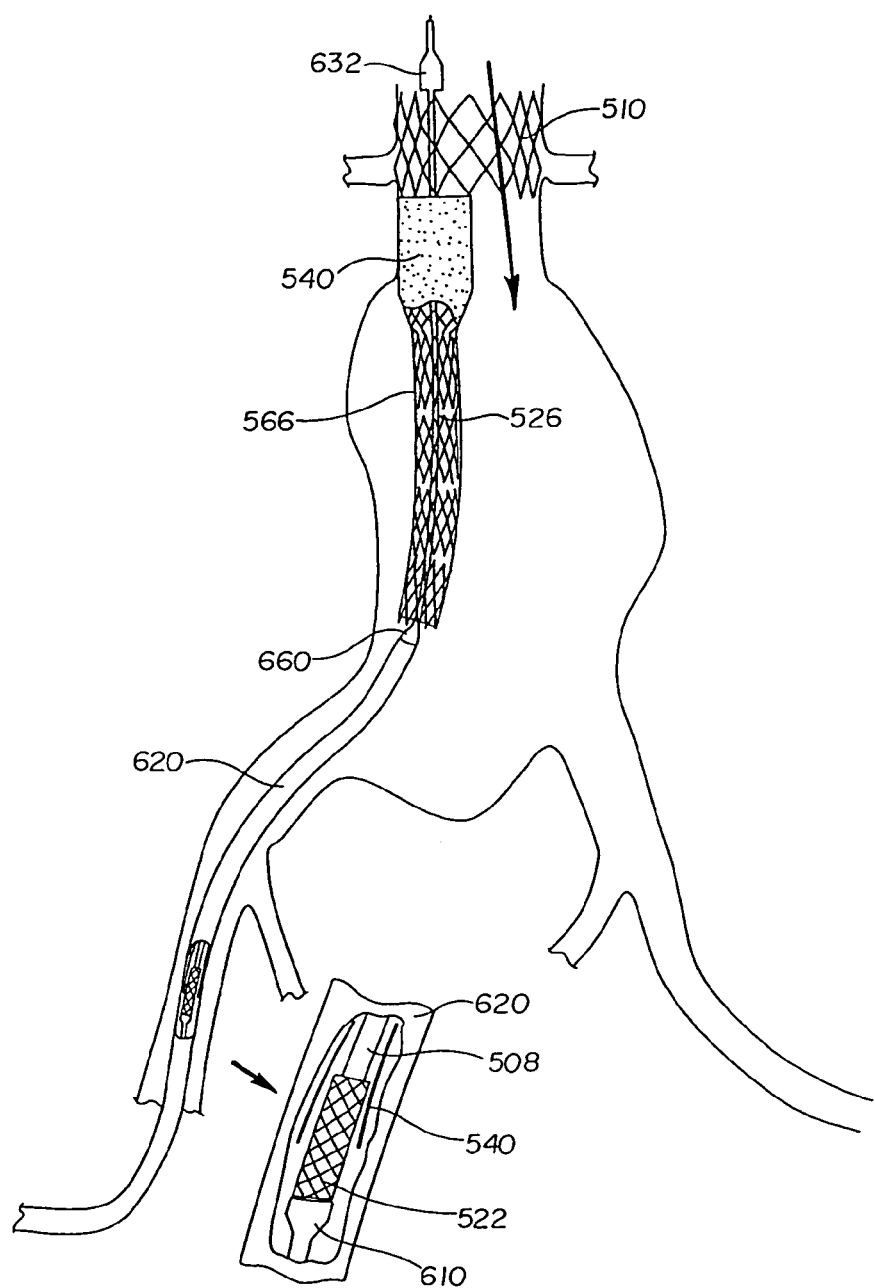

Main sheath 620 is further withdrawn in FIG. 16, showing the upper graft segment 566 deployed. Since main sheath 620 covers support stents 526 its retraction causes them to expand. A plurality of support stents 526 are pre-loaded in the delivery catheter. Each is pre-attached to either the upper or lower graft segment depending on its location. In between the support stents there may be support stent buttresses to maintain the correct position of the support stents during deployment. The end of main sheath 620 is atop secondary bulb 660 which provides a smooth transition allowing main sheath 620 to be re-advanced smoothly into the upper graft segment.

Figure 17:
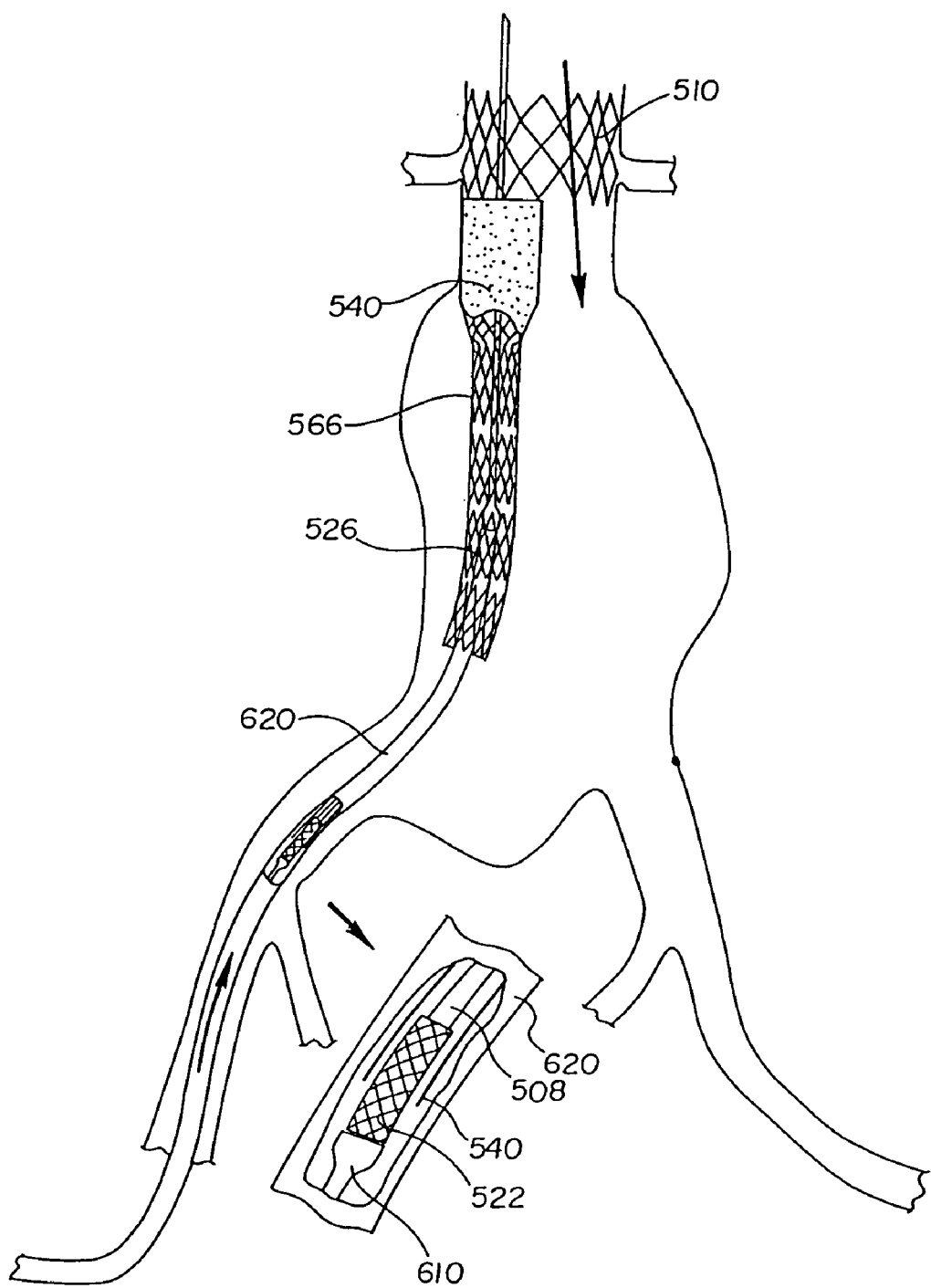
Figure 18:
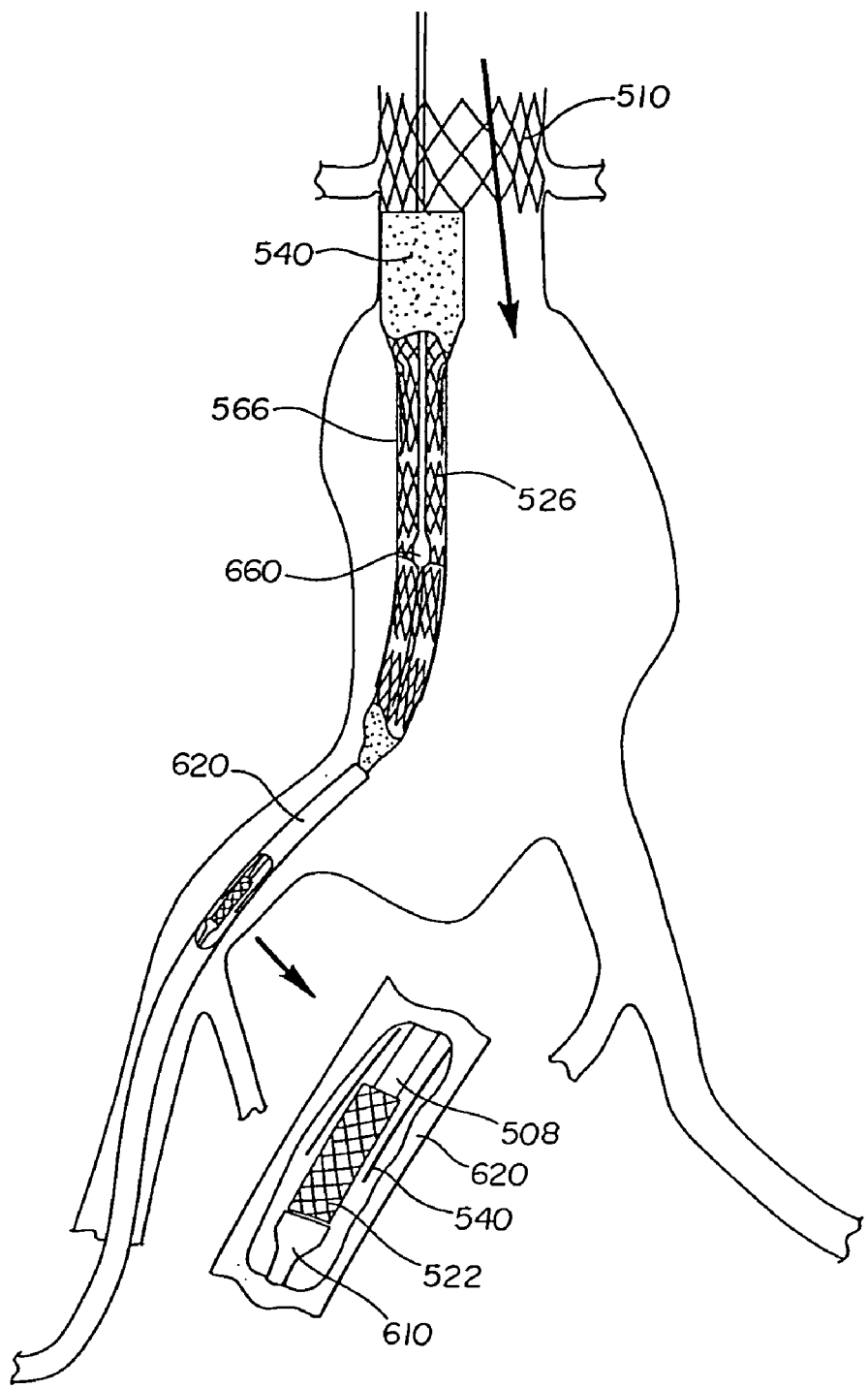
Figure 19:
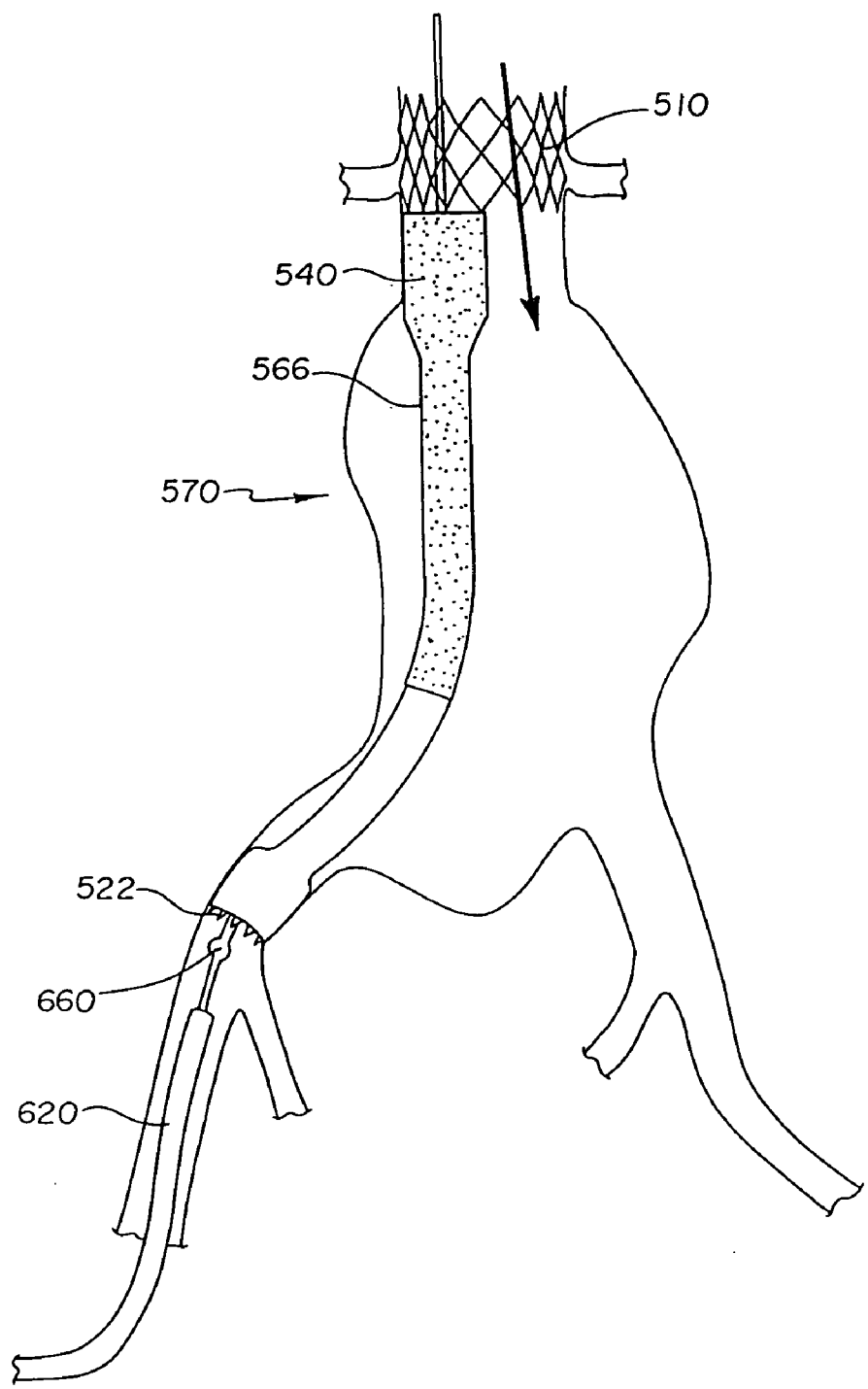

After deployment of upper graft segment 566, the entire delivery system is advanced cranially until the iliac stent 522 is in proper position relative to the internal iliac artery, as shown in FIG. 17. Injection of radiographic contrast solution aids in positioning the iliac stent. After positioning of iliac stent 522, main sheath 620 is further withdrawn, allowing the lower graft segment to deploy within the upper segment as shown in FIG. 18. FIG. 19 shows leg 570 fully deployed and main sheath 620 being removed through the external iliac artery.

The second leg of the graft system is identical to the first leg except with respect to the aortic stent and is deployed in a similar manner once the aortic stents are properly aligned with one another in a manner similar to that described with respect to the other embodiments.

What is claimed is:

1. A graft system for repairing an abdominal aortic aneurysm comprising a one-piece tubular graft component defining a single flow channel and having a first end portion, a second end portion, and a middle portion extending therebetween, the first end portion including an aortic stent having an O-shaped portion and a D-shaped portion, the middle portion including a plurality of independent grasping stents spaced apart from one another and configured to prevent migration of the graft component once deployed, the second end portion including an iliac stent, wherein the cross-sectional areas of the D-shaped portion of the aortic stent and the iliac stent are greater than the cross-sectional area of the middle portion and the one-piece graft component tapers from the first and second end portions to the middle portion.

2. The graft system of claim 1 wherein the tubular graft component further includes a length adjustment element.

3. The graft system of claim 2 wherein the length adjustment element comprises a bellows region within the middle portion.

* * * * *